(12) United States Patent
Zudak et al.

(10) Patent No.: US 12,737,886 B2
(45) Date of Patent: Sep. 15, 2026

(54) LESION MAPPING ASSISTANT SYSTEM AND METHOD

(71) Applicant: Thalocan Research Innovations LLC, Indianapolis, IN (US)

(72) Inventors: Eric Zudak, Indianapolis, IN (US); Cyrus Mirakhor, West Hollywood, CA (US); Paul Stroili, Skokie, IL (US)

(73) Assignee: Thalocan Research Innovations LLC, Indianapolis, IN (US)

( * ) Notice: Subject to any disclaimer, the term of this patent is extended or adjusted under 35 U.S.C. 154(b) by 0 days.

(21) Appl. No.: 19/266,533

(22) Filed: Jul. 11, 2025

(65) Prior Publication Data

US 2026/0051051 A1 Feb. 19, 2026

Related U.S. Application Data

(63) Continuation of application No. 18/805,248, filed on Aug. 14, 2024.

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/30096* (2013.01)

(58) Field of Classification Search
CPC ........ G06T 7/0012; G06T 2207/30096; G16H 30/40
See application file for complete search history.

(56) References Cited

U.S. PATENT DOCUMENTS

2016/0250519 A1* 9/2016 Watterson .......... A63B 24/0084 482/4
2021/0012493 A1* 1/2021 Jiang ...................... G16H 30/40
2022/0096853 A1 3/2022 Bakalo et al.
2023/0284968 A1* 9/2023 Toews .................... A61B 1/227
2024/0177836 A1* 5/2024 Paik ....................... A61B 5/742

FOREIGN PATENT DOCUMENTS

CA 3073259 A1 * 2/2019 ........... A61B 5/0064
JP 2003513735 A * 4/2003 ........... A61B 5/0059
KR 10-2064957 B1 10/2019
WO 2011-116314 A1 9/2011

OTHER PUBLICATIONS

Song B, et al., *Smartphone-Based LiDAR Application for Easy and Accurate Wound Size Measurement*, J Clin Med. Sep. 19, 2023, 12(18):6042; DOI: 10.3390/jcm12186042; PMID: 37762982; PMCID: PMC10531604; (abstract) 2 pages.
International Search Report and Written Opinion issued by the Ministry of Intellectual Property (Republic of Korea) on Dec. 9, 2025 for corresponding PCT Application No. PCT/US2025/042050, 8 pages.

* cited by examiner

*Primary Examiner* — Khai M Nguyen
(74) *Attorney, Agent, or Firm* — Womble Bond Dickinson US LLP

(57) ABSTRACT

A method for mapping one or more cutaneous conditions of a cutaneous surface may include: identifying a body map; identifying one or more body regions corresponding to the body map; identifying at least one representation corresponding to the one or more body regions; identifying one or more icons corresponding to the at least one representation;
and defining the one or more icons on the at least one representation.

28 Claims, 27 Drawing Sheets
(21 of 27 Drawing Sheet(s) Filed in Color)

LESION MAPPING ASSISTANT SYSTEM AND METHOD

CROSS REFERENCE TO RELATED APPLICATIONS

This application is a continuation of U.S. patent application Ser. No. 18/805,248, filed on Aug. 14, 2024, the entire content of which is incorporated herein by reference.

BACKGROUND

1. Field

Aspects of the present disclosure relate to systems and methods for mapping one or more cutaneous conditions of a cutaneous surface.

2. Description of the Related Art

In the field of dermatology, present methods of mapping cutaneous conditions, such as lesions, nodules, papules, discolored patches, and other relevant cutaneous abnormalities, face several limitations. Typically, such methods rely on visual assessments of the affected area, which are subjective, and prone to human error.

Further, notes of such visual assessments are often recorded manually, for e.g., via pen and paper, which can lack in detail and nuance. Moreover, the characteristics (e.g., size, shape, count, location, color, etc.) of cutaneous conditions continuously change over time. Consequently, present methods may overlook subtle changes in these characteristics, which may result in inconsistent and inaccurate diagnosis and treatment.

Moreover, many diseases use the percentage of involvement as a severity criteria. The clinician will estimate the percentage by observing a bodily region (trunk, lower extremities, head, etc., to determine the extent of involvement. The various current methods used for such estimation are not precise and introduce a high degree of subjectivity to the calculation. Further if the assessment is made by more than one person during the course of a study, the question of differences in the subjective estimation introduces further uncertainty into the reliability of any assessment of the ongoing progression of the disease.

Further, placebo controls in research studies directed to the study of cutaneous conditions, are negatively impacted by the shortcomings of such methods of visual assessments. For example, because such methods of visual assessment are conducted in a subjective and disjointed manner, they may over count or under count the occurrence of cutaneous conditions, leading to inaccurate measurement of placebo effects. Also, placebo control groups may be analyzed inconsistently during the course of research studies. This may further lead to inaccurate placebo control outcomes, thereby jeopardizing the entirety of the research studies.

Additionally, the visual assessment traditionally involves analyzing images of the patient's body, including images depicting sensitive regions of the patient's body, which may negatively impact the patient's privacy. For example, the images may further include identifying characteristics that could be used to identify the patient, thus putting the patient's privacy in jeopardy.

Furthermore, if a patient requires medical intervention while under observation during a research study, the patient is ordinarily removed from the research study so that the required medical intervention may be performed. However, such medical intervention is ordinarily untracked, which may lead to errors and/or discrepancy in the outcome of the research study, and may even prevent the patient from continuing with the research study once the medical intervention has been performed.

In particular, patients afflicted with cutaneous conditions having an irregular shape, such as Hidradenitis Suppurativa (HS), are often evaluated incorrectly due to the variable nature of such cutaneous conditions. An analysis of such a cutaneous condition during an initial medical evaluation may not conform to the analysis performed during a subsequent medical evaluation, because the characteristics of the cutaneous condition change irregularly.

Additionally, the lack of an accessible central repository of past assessments of the affected area may result in further inconsistency and inaccuracy, especially if different healthcare providers are involved in diagnosis and treatment. Accordingly, a need exists for improving present methods of assessing cutaneous conditions. It is with respect to this need, that aspects of the present disclosure are directed.

The above information disclosed in this Background section is for enhancement of understanding of the background of the present disclosure, and, therefore, it may contain information that does not constitute prior art.

SUMMARY

According to an aspect, a system for mapping one or more cutaneous conditions of a cutaneous surface may include: at least one processor, at least one display, the at least one display configured to receive user input, and operatively connected to the at least one processor; and a memory, the memory operatively connected to the at least one processor and storing instructions that, when executed, cause the at least one processor to perform a method, the method including: identifying a body map; identifying one or more body regions corresponding to the body map; identifying at least one representation corresponding to the one or more body regions; identifying one or more icons corresponding to the at least one representation; and defining the one or more icons on the at least one representation.

According to another aspect, the system for mapping the one or more cutaneous conditions of the cutaneous surface may further include: at least one camera, the at least one camera operatively connected to the at least one processor.

According to an aspect, a method for mapping one or more cutaneous conditions of a cutaneous surface may include: identifying a body map; identifying one or more body regions corresponding to the body map; identifying at least one representation corresponding to the one or more body regions; identifying one or more icons corresponding to the at least one representation; and defining the one or more icons on the at least one representation.

According to another aspect, the body map may include one or more multi-dimensional renderings.

According to another aspect, the at least one representation may include one or more images.

According to another aspect, the identifying the body map may include: identifying a patient profile; and generating the body map based on the patient profile.

According to another aspect, the identifying the one or more body regions may include: detecting the one or more body regions based on the body map; and defining the one or more body regions on the body map.

According to another aspect, the identifying the one or more icons may include: generating the one or more icons;

and rendering the one or more icons while simultaneously rendering the at least one representation.

According to another aspect, the identifying the one or more icons may include: detecting the one or more icons from a selection of icons; and rendering the one or more icons while simultaneously rendering the at least one representation.

According to another aspect, the defining the one or more icons may include:

detecting a placement of the one or more icons; and overlaying the one or more icons on the at least one representation based on the placement of the one or more icons.

According to another aspect, the at least one representation may be captured by at least one camera.

According to another aspect, the at least one representation may include at least one of a captured representation or default representation.

According to an aspect, a method for mapping one or more cutaneous conditions of a cutaneous surface may include: identifying a cutaneous surface on a patient having a cutaneous condition; identifying a default representation, the default representation corresponding to the cutaneous surface; and mapping the one or more cutaneous conditions on the cutaneous surface using the default representation.

According to another aspect, the identifying the default representation may include: identifying one or more patient details; and selecting a default representation aligned with the one or more patient details, the default representation including an image.

According to another aspect, the identifying the default representation may include: capturing a first image of the cutaneous surface; and modifying the first image to generate a second image, the second image being configured to protect one or more patient details, wherein the default representation includes the second image.

According to another aspect, the modifying the first image includes blurring one or more portions of the first image.

According to an aspect, a method for mapping one or more cutaneous conditions of a cutaneous surface may include: identifying a first representation corresponding to one or more body regions of the cutaneous surface; identifying a second representation corresponding to the one or more body regions of the cutaneous surface; identifying a ghost representation based on the first representation; overlaying the ghost representation on the second representation of the cutaneous surface; and mapping the one or more cutaneous conditions using the ghost representation overlayed on the second representation.

According to another aspect, the ghost representation may include one or more images.

According to another aspect, the first representation may include one or more images.

According to another aspect, the second representation may include one or more images.

According to an aspect, a method for mapping one or more cutaneous conditions of a cutaneous surface may include: identifying at least one of a first captured representation or a first default representation, the at least one of the first captured representation or the first default representation corresponding to a first evaluation; identifying at least one of a second captured representation or a second default representation, the at least one of the second captured representation or the second default representation corresponding to a second evaluation; and rendering the at least one of the first captured representation or the first default representation and the at least one of the second captured representation or the second default representation.

According to another aspect, the at least one of the first captured representation or the first default representation may be selectively rendered with the at least one of the second captured representation or the second default representation based on user input.

According to another aspect, the at least one of the first captured representation or the first default representation may be simultaneously rendered with the at least one of the second captured representation or the second default representation based on user input.

This summary is provided to introduce a selection of features and concepts of example embodiments of the present disclosure that are further described below in the detailed description. This summary is not intended to identify key or essential features of the claimed subject matter nor is it intended to be used in limiting the scope of the claimed subject matter. One or more of the described features according to one or more examples may be combined with one or more other described features according to one or more examples to provide a workable method or device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings, together with the specification, illustrate non-limiting and non-exhaustive examples of the present disclosure.

DETAILED DESCRIPTION

Figure 1:
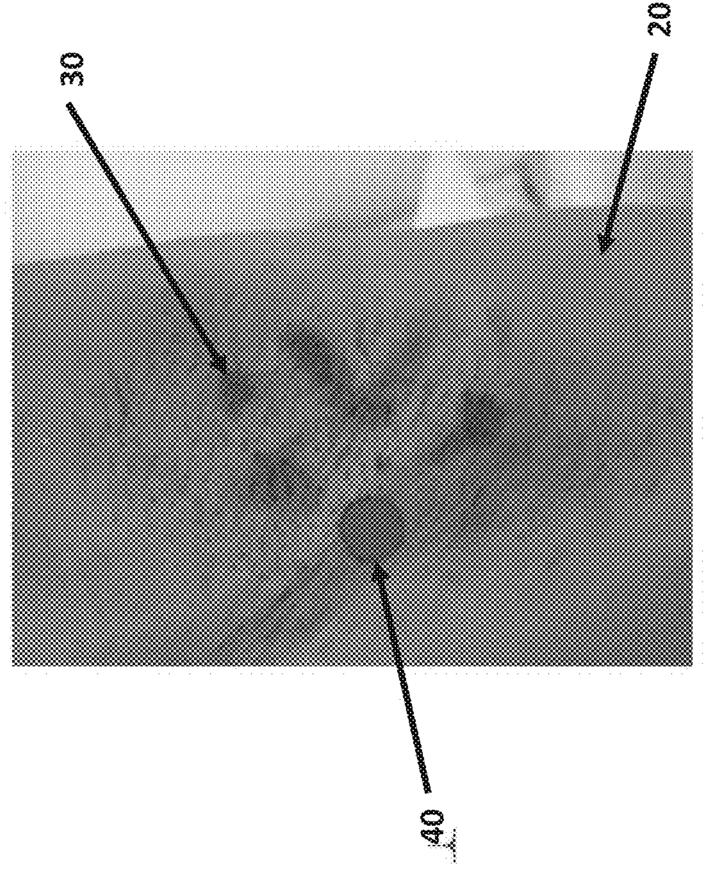
FIG. 1 depicts a frontal view of an example cutaneous surface having one or more measurement markers, according to some examples.

Features of the inventive concept and methods of accomplishing the same may be understood more readily by reference to the following detailed description of example embodiments and the accompanying drawings. Hereinafter, example embodiments will be described in more detail with reference to the accompanying drawings. The present invention, however, may be embodied in various different forms, and should not be construed as being limited to only the illustrated example embodiments herein. Rather, these example embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. Further, parts not related to the description of the example embodiments might not be shown to make the description clear. In the drawings, the relative sizes of elements, layers, and regions may be exaggerated for clarity.

In the following description, for the purposes of explanation, numerous specific details are set forth to provide a thorough understanding of various example embodiments. It is apparent, however, that various example embodiments may be practiced without these specific details or with one or more equivalent arrangements.

When a certain example embodiment may be implemented differently, a specific process order may be performed differently from the described order. For example, two consecutively described processes may be performed substantially at the same time or performed in an order opposite to the described order.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Systems and methods for mapping one or more cutaneous conditions of a cutaneous surface will now be described herein with reference to the figures.

FIG. 1 depicts a frontal view of an example cutaneous surface 20 having one or more measurement markers according to one or more examples of the present disclosure. In an illustrative example, the cutaneous surface 20 may include multiple measurement markers, including the measurement marker 40.

Referring to FIG. 1, the cutaneous surface may further include one or more cutaneous conditions. In an illustrative example, the cutaneous surface 20 may include multiple cutaneous conditions, including the cutaneous condition 30.

Figure 2:
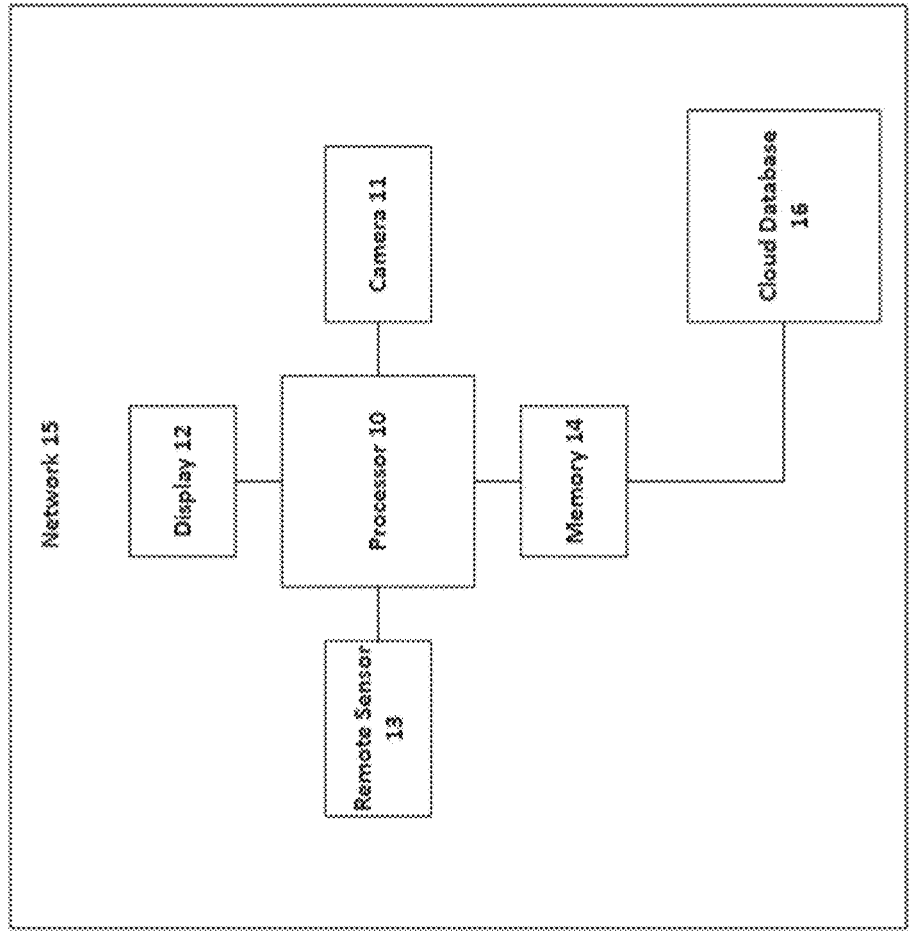
FIG. 2 depicts a block diagram including an example system for mapping one or more cutaneous conditions of a cutaneous surface, according to some examples.

FIG. 2 depicts a block diagram illustrating an example system for mapping one or more cutaneous conditions of a cutaneous surface of the cutaneous surface.

Referring to FIG. 2, the system may include a processor 10 that may be operatively connected to a memory 14. For example, the memory 14 may be operatively connected to the processor 10 via a network 15. In other examples, the processor 10 and the memory 14 may be integrated as a single system (for e.g., as a personal cellular device).

As shown in FIG. 2, the processor 10 may be operatively connected to a camera 11. For example, the camera 11 may be operatively connected to the processor 10 via a network 15. In further examples, the processor 10, the memory 14 and the camera 11, or any combination thereof, may be integrated as a single system (for e.g., as a personal cellular device).

In another example, the camera 11 may be configured to capture a representation, for example, a visual representation (for e.g., a digital image) of the cutaneous surface 20 when executing instructions stored in the memory 14.

In another example, the camera 11 may include at least one processor and at least one memory that may be operatively connected to the processor 10 and the memory 14. For example, the at least one processor and at least one memory of the camera 11 may be operatively connected to the processor 10 and the memory 14 via the network 15.

In some examples, the at least one processor of the camera 11 may be configured to store a visual representation captured by the camera 11 in the at least one memory of the camera 11. For example, the visual representation captured by the camera 11 may be stored (for e.g., temporarily stored) in the at least one memory of the camera 11. In further examples, the at least one processor of the camera 11 may communicate the visual representation captured by the camera 11 stored in the at least one memory of the camera 11 to the memory 14, for example, via the network 15.

As shown in FIG. 2, the processor 10 may be operatively connected to a display 12. For example, the display 12 may be configured to communicate with the processor 10 via the network 15. In other examples, the processor 10, the memory 14, the camera 11 and the display 12, or any combination thereof, may be integrated as a single system (for e.g., as a personal cellular device). The processor 10 may include the display 12 and may also include other output device(s) such as speakers, a printer, etc. The aforementioned devices are examples and others may be used.

In another example, the display 12 may be configured to receive user input (for e.g., a capacitive touch display). In other examples, the processor 10 may further be operatively connected to other input devices such as a keyboard, a mouse, a pen, a sound input device, a touch input device, etc.

In another example, the processor 10 may store the user input received by the display 12 in the memory 14.

As shown in FIG. 2, the processor 10 may be operatively connected to a remote sensor 13. For example, the remote sensor 13 may be operatively connected to the processor 10 via the network 15. In further examples, the processor 10, the memory 14, the camera 11, the display 12 and the remote sensor 13, or any combination thereof, may be integrated as a single system (for e.g., as a personal cellular device).

In another example, the remote sensor 13 may be configured to detect characteristics (for e.g., height and density) of the cutaneous condition 30 and/or the measurement marker 40 present on the cutaneous surface 20. For example, the remote sensor 13 may be a light detection and ranging (LiDAR) sensor, which may be used to compile a 3-D digital map of the cutaneous surface 20.

In another example, the remote sensor 13 may be configured to capture a representation, for example, a topographic representation (for e.g., a three-dimensional digital image) of the cutaneous surface 20 when executing instructions stored in the memory 14.

In some examples, the remote sensor 13 may include at least one processor and at least one memory that may be operatively connected to the processor 10 and the memory 14. For example, the at least one processor of the remote sensor 13 may be configured to store a topographic representation captured by the remote sensor 13 in the at least one memory of the camera 11. In further examples, the topographic representation captured by the remote sensor 13 may be stored (for e.g., temporarily stored) in the at least one memory of the remote sensor 13. In other examples, the at least one processor of the remote sensor 13 may communicate the topographic representation captured by the remote sensor 13 stored in the at least one memory of the remote sensor 13 to the memory 14, for example, via the network 15.

As shown in FIG. 2, the memory 14 may be configured to communicate with the processor 10 via the network 15. In some examples, the memory 14 may comprise a volatile storage (for e.g., random access memory), non-volatile storage (for e.g., read-only memory), flash memory, or any combination thereof. The memory 14 may be configured to store a one or more representations captured by the camera 11. The memory 14 may further be configured to store one or more topographic representations captured by the remote sensor 13.

In another example, the processor 10 and/or the memory 14 may be communicatively coupled to other processors and/or other memory devices via a communication medium, such as via the network 15. In some examples, the communication medium may include, without limitation, RF transmitter, receiver, and/or transceiver circuitry; universal serial bus (USB), parallel, and/or serial ports, or any combination thereof.

In another example, the memory 14 and/or the processor 10 may further be communicatively coupled with a cloud database 16. For example, the memory 14 may be communicatively coupled with a cloud database 16 via the network 15. In other examples, the memory 14 may be communicatively coupled with a cloud database 16 via any applicable wireless and/or wired communication means.

In some examples, the processor 10 may communicate data stored in the memory 14 to the cloud database 16. The cloud database 16 may store the communicated data.

In another example, the processor 10 may receive data from the cloud database 16 to store in the memory 14.

In another example, the memory 14 may further be configured to store one or more software applications such as the mapping system 500 (the "system 500"). The system 500 may include instructions that, when executed by the processor 10, cause the system to perform the methods described herein to determine characteristics of one or more cutaneous conditions, including the cutaneous condition 30 present on the cutaneous surface 20.

Figure 3:
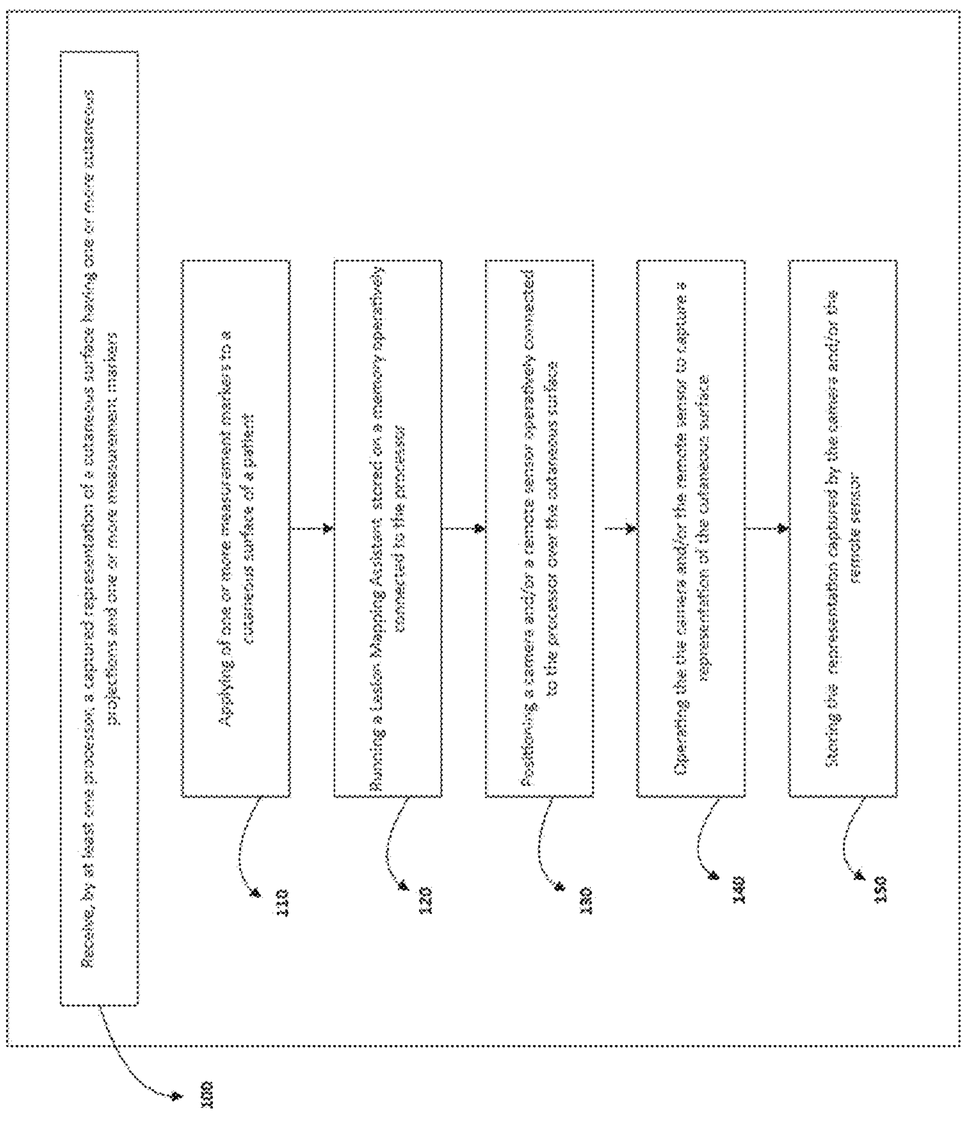
FIG. 3 depicts a flowchart including an example method to receive, by at least one processor, a captured representation of a cutaneous surface having one or more cutaneous conditions and one or more measurement markers, according to some examples.

FIG. 3 depicts a flowchart including an example method 100 to receive, by at least one processor, a captured representation of a cutaneous surface having one or more cutaneous conditions and one or more measurement markers. The method 100 may include a first process 110 of applying one or more measurement markers on a cutaneous surface of a patient. In an illustrative example, the measurement marker 40 may be placed by a user, for e.g., a clinician, onto the cutaneous surface 20 having the cutaneous condition 30. This may be accomplished by including an adhesive backing on a sticker that allows it to be adhered to the skin at least temporarily. Alternatively, the placement of a marking on the cutaneous surface 20 may be accomplished through use of a permanent marking technique, such as a tattoo, or through use of a semi-permanent marking technique, such as through use of an indelible marker. Advantage may also be taken of naturally occurring distinctive features on the cutaneous surface 20 that are likely to remain unchanged, such as moles, freckles, or body parts like a nipple or navel, if those distinctive features are located near the cutaneous surface under examination. If more than one measurement marker is to be used, a combination of these various types of markers may be employed. Further, the system 500 may be configured to allow a clinician to adjust characteristics of the measurement marker(s) (e.g., measurement marker 40), including, but not limited to the size of the measurement marker(s) (e.g., length, width, area, or the like), the shape of the measurement marker(s) (e.g., perimeter or the like), and/or the like. For example, upon placing a measurement marker, the clinician may be prompted by the system 500 (e.g., via the display 12) to input and/or adjust characteristics of the measurement marker, such as an area of the measurement marker, whereupon the clinician may then interact with the system 500, such as via the display 12 to input and/or adjust the area of measurement marker.

In some examples, in addition to prompting the clinician to input and/or adjust characteristics of the measurement marker, the system 500 may be configured to further display detected characteristics of the measurement marker. For example, the system 500 may detect characteristics of the measurement marker based on input received via the camera 11, such as images and/or video feeds of the measurement marker that is placed by the clinician. The system 500 may, via AI/ML algorithms, analyze the images and/or video feeds of the measurement marker, and detect characteristics of the measurement marker based on the analysis, such as an area of the measurement marker. The system 500 may display the detected characteristics of the measurement marker, and allow the clinician to adjust the detected characteristics, such as via the display 12.

Referring to FIG. 3, the method 100 may include a second process 120 of running the system 500 stored on a memory operatively connected to a processor. In an illustrative example, the system 500 may be stored on the memory 14 operatively connected to the processor 10. In further examples, the processor 10 may be caused to operate the system 500 by a user, for e.g., a clinician.

In another example, the method 100 may include a third process 130 of positioning a camera and/or a remote sensor over the cutaneous surface. In an illustrative example, the camera 11 and/or the remote sensor 13 may be positioned over the cutaneous surface by a user, for e.g., a clinician, so that the measurement marker 40 and the cutaneous condition 30 are within the capturing area of the camera 11 and/or the remote sensor 13.

In another example, the method 100 may include a fourth process 140 of operating the camera and/or the remote sensor to capture a representation of the cutaneous surface having the one or more measurement markers. In an illustrative example, the camera 11 and/or a remote sensor 13 may be operated by a user, for e.g., a clinician, to capture a representation of the cutaneous surface 20 having the measurement marker 40 and the cutaneous condition 30.

In another example, the method 100 may include a fifth process 150 of storing the representation captured by the camera and/or the remote sensor. In an illustrative example, the captured representation 50 captured by the camera 11 and/or the remote sensor 13 may be stored, for e.g., in the memory 14 via the processor 10.

Figure 4:
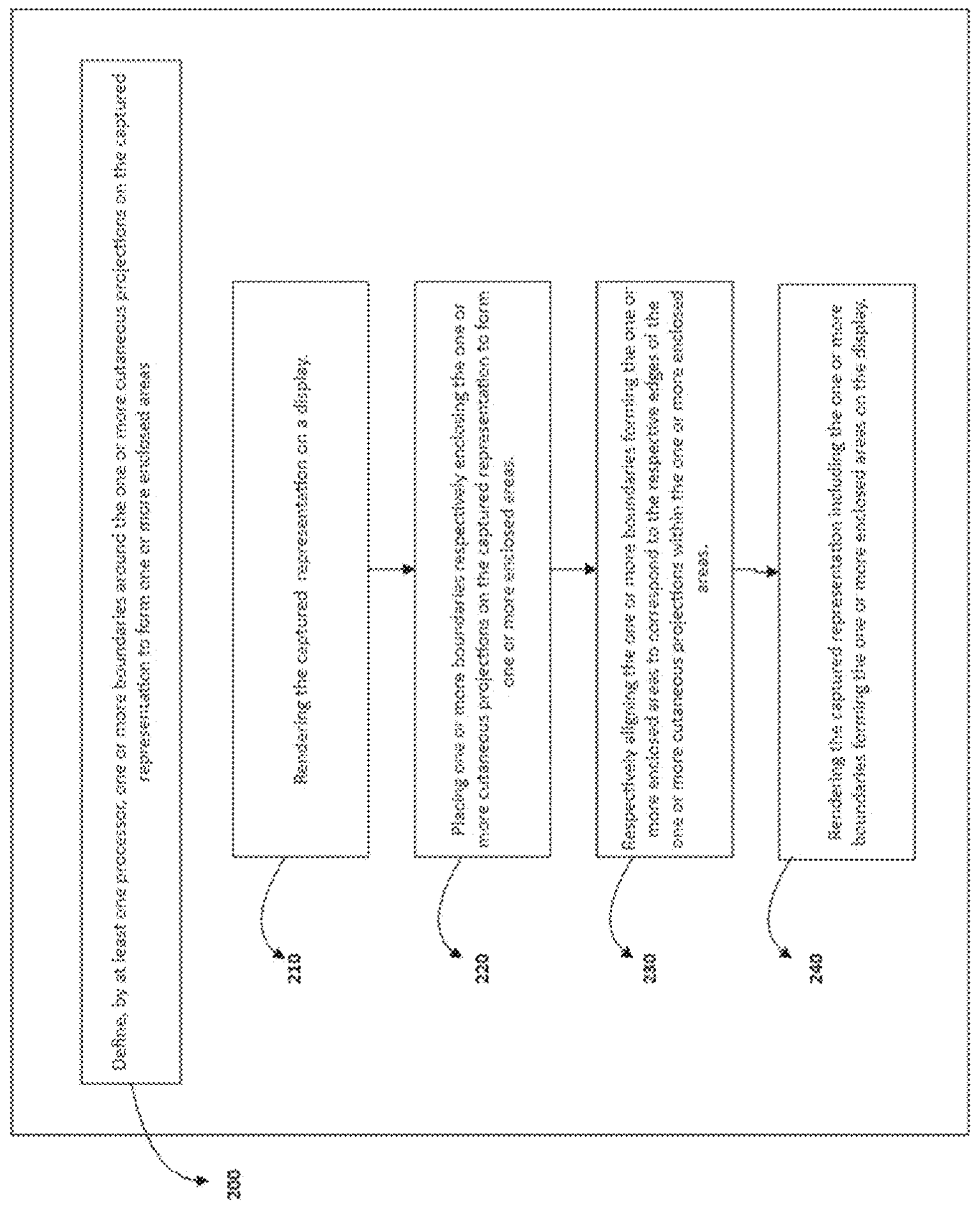
FIG. 4 depicts a flowchart including an example method to define, by the at least one processor, one or more boundaries around the one or more cutaneous conditions on the captured representation to form one or more enclosed areas, according to some examples.

FIG. 4 depicts a flowchart including an example method 200 to define, by at least one processor, one or more boundaries around the one or more cutaneous conditions on the captured representation to form one or more enclosed areas. The method 200 may include a first process 210 of rendering the captured representation on a display. In an illustrative example, the captured representation 50 may be rendered, for example, on the display 12.

Figure 8:
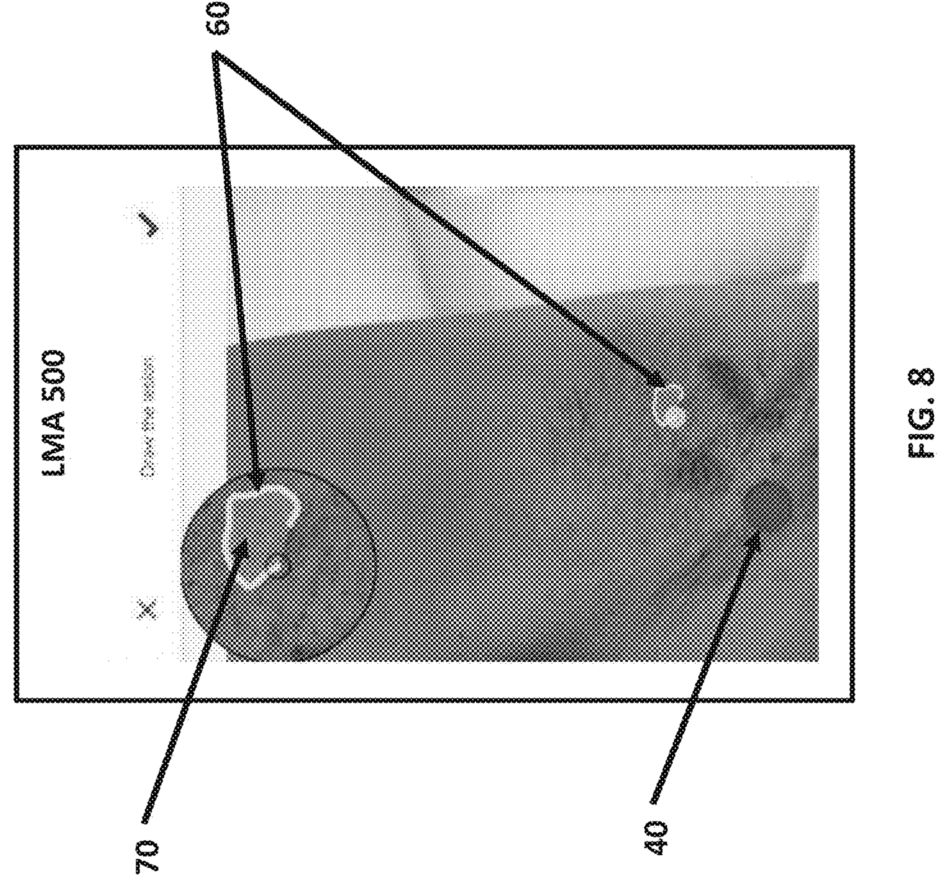
FIG. 8 depicts the one or more boundaries forming the one or more enclosed areas of FIG. 4, according to some examples.

Referring to FIGS. 4 and 8, the method 200 may include a second process 220 of placing one or more boundaries respectively enclosing the one or more cutaneous conditions on the captured representation to form one or more enclosed areas. In further examples, the one or more cutaneous conditions may be respectively enclosed within the one or more enclosed areas.

In an illustrative example, the system 500 may allow a user, for e.g., a clinician, to interact with the display 12 (for e.g., via a capacitive-touch based display) to place a boundary 60 around the cutaneous condition 30. The user may input the boundary 60 on the display 12, for e.g., via placing their finger(s) on the display, such that the boundary corresponds to the edges of the cutaneous condition 30 rendered on the display 12.

In another example, the placement of the boundary 60 may be accomplished physically through use of a marking technique, such as through use of a semi-permanent marking technique, such as through use of an indelible marker on the cutaneous surface 20.

In another example, the method 200 may include a third process 230 of aligning the one or more boundaries forming the one or more enclosed areas to correspond to the edges of the one or more cutaneous conditions within the one or more enclosed areas. In an illustrative example, the system 500 may cause the processor 10 to align the boundary 60 to correspond to the edges of the cutaneous condition 30 within the enclosed area 70.

In another example, the second process 220 and the third process 230 may be performed by the system contemporaneously and/or simultaneously. For example, the user may interact with the at least one display to place one or more points on the captured representation that correspond to the edges of a cutaneous condition of the one or more cutaneous conditions. The system may then, based on the one or more points placed by the user, form a boundary on the captured representation to enclose the cutaneous condition.

In another example, the method 200 may include a fourth process 240 of rendering the captured representation including the one or more boundaries forming the one or more enclosed areas on the display. In an illustrative example, the captured representation 50 including the boundary 60 may be rendered on the display 12. In further examples, the captured representation 50 including the boundary 60 may be contemporaneously rendered on the display 12 while the user manually places the boundary 60 around the cutaneous condition 30.

Figure 5:
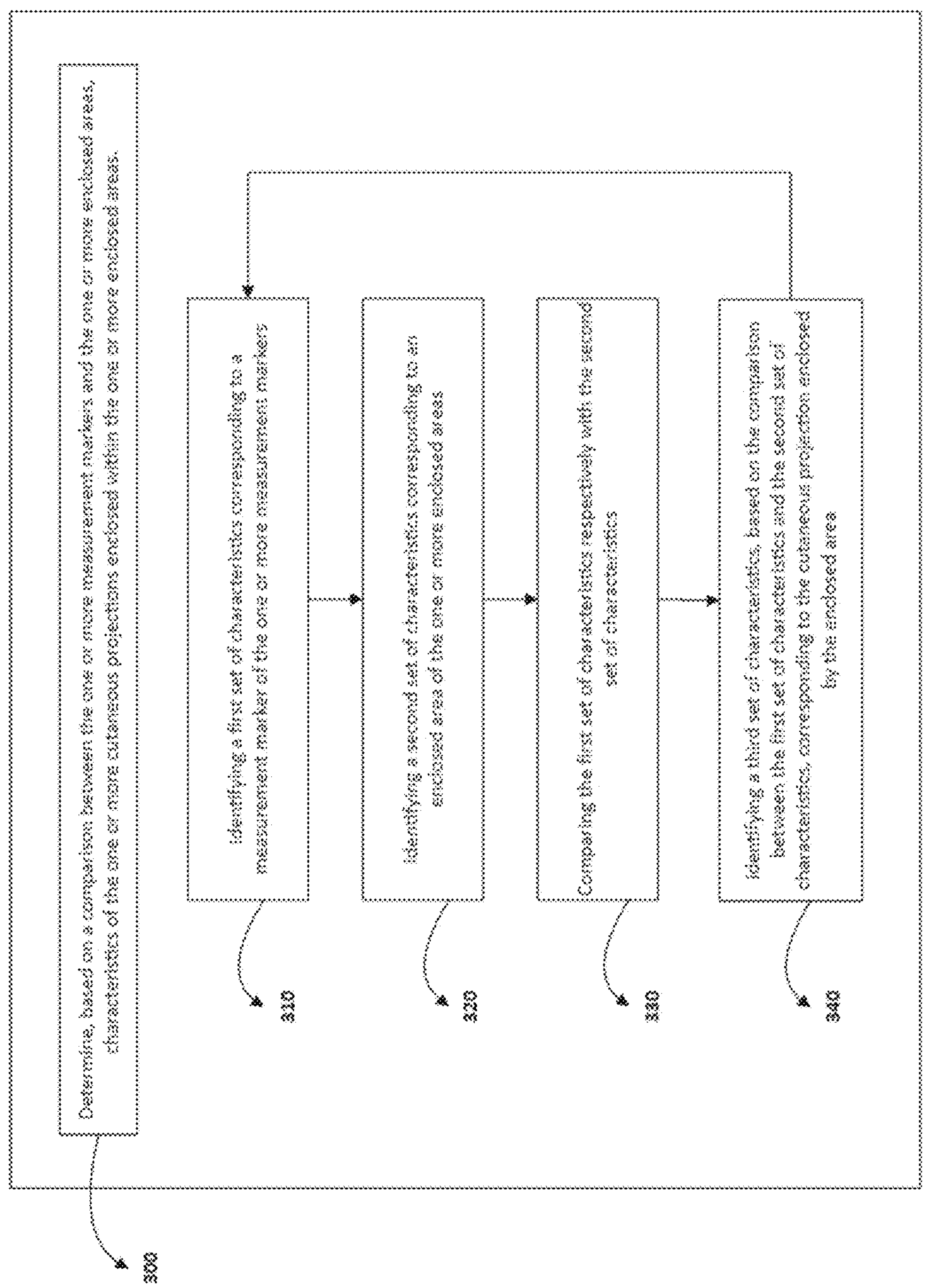
FIG. 5 depicts a flowchart including an example method to determine, by the at least one processor and based on a comparison between the one or more measurement markers and the one or more enclosed areas, characteristics of the one or more cutaneous conditions enclosed within the one or more enclosed areas, according to some examples.

FIG. 5 depicts a flowchart including an example method 300 to determine, based on a comparison between the one or more measurement markers and the one or more enclosed areas, characteristics of the one or more cutaneous conditions enclosed within the one or more enclosed areas. That is, characteristics of the one or more cutaneous conditions may be determined by comparing those characteristics for the cutaneous conditions to those same characteristics for the measurement markers, those characteristics for the measurement markers being a known value or quantity.

Referring to FIG. 5, the method 300 may include a first process 310 of identifying a first set of characteristics corresponding to a measurement marker of the one or more measurement markers. The first set of characteristics may comprise quantitative and/or qualitative values of the size, shape, color, or any other applicable characteristics of the measurement marker. In an illustrative example, the system 500 may cause the processor 10 to determine a first set of characteristics of the measurement marker 40. This may allow the system 500 to establish a correlation between the known characteristics of the measurement markers and how those characteristics are measured by the system to establish one or more reference points for the system.

In further examples, the system 500, via the at least one processor and the at least one display, may allow a user of the system 500 to change quantitative and/or qualitative values of the size, shape, color, or any other applicable characteristics of a measurement marker of the one or more measurement markers. In an illustrative example, a user of the system 500, for e.g., a clinician, may interact with the display 12 to manually change the quantitative and/or qualitative values of the first set of characteristics that correspond to the measurement marker 40 determined by the processor 10.

In another example, the method 300 may include a second process 320 of identifying a second set of characteristics corresponding to an enclosed area of the one or more enclosed areas. The second set of characteristics may comprise quantitative and/or qualitative values of the size, shape, color, or any other applicable characteristics of the enclosed area. In an illustrative example, the system 500 may cause the processor 10 to identify a second set of characteristics corresponding to the enclosed area 70.

In another example, the method 300 may include a third process 330 of comparing the first set of characteristics with the second set of characteristics.

In another example, the method 300 may include a fourth process 340 of identifying a third set of characteristics based on the comparison between the first set of characteristics and the second set of characteristics, the third set of characteristics corresponding to the cutaneous condition enclosed by the enclosed area. The third set of characteristics may comprise quantitative and/or qualitative values of the size, shape, color, or any other applicable characteristics of the cutaneous conditions within the enclosed area. In an illustrative example, the system 500 may cause the processor 10 to identify a third set of characteristics corresponding to the cutaneous condition 30 within the enclosed area 70.

In another example, steps of the method 300 may be repeated separately and/or contemporaneously for each of the one or more cutaneous conditions enclosed by the one or more enclosed areas to respectively identify the corresponding one or more third sets of characteristics.

Figure 11:
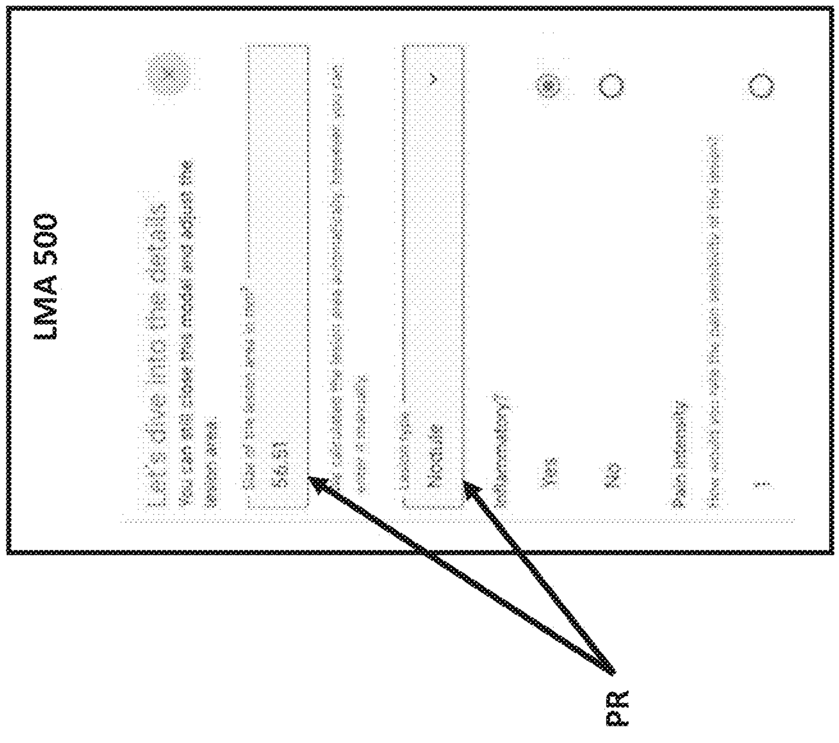
FIG. 11 depicts interactive prompts generated by the system, according to some examples.

In another example, the system 500 may allow a user to interact with the display, such that the user is able to change any information, including any values and/or quantities, of the determined sets of characteristics of the one or more lesions of the cutaneous surface. In an illustrative example, the system 500 may allow a user to interact with the display 12 to modify values and/or quantities of the determined third set of characteristics of the cutaneous condition 30, as depicted in FIG. 11.

Figure 6:
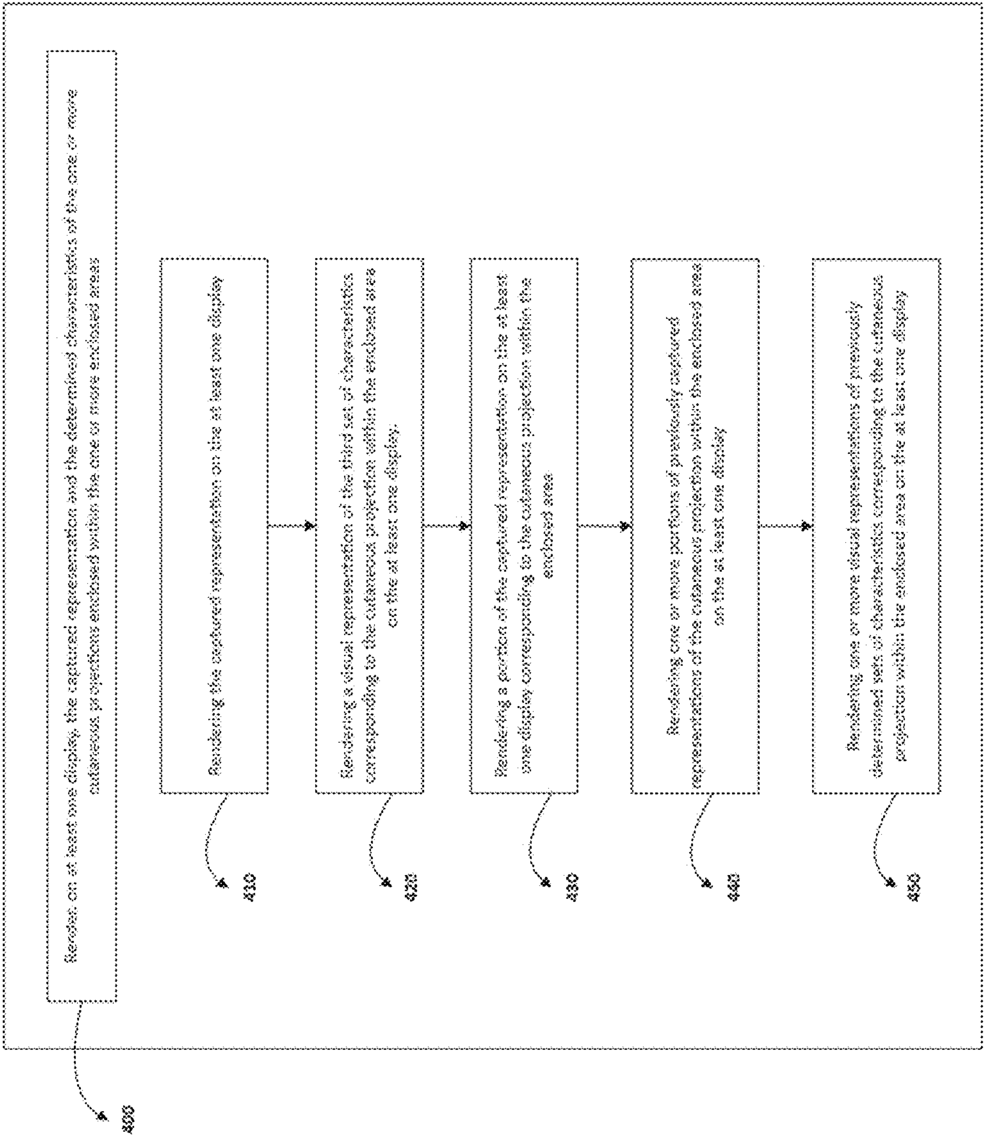
FIG. 6 depicts a flowchart including an example method for rendering, by the at least one processor on at least one display, the captured representation, and the determined characteristics of the one or more cutaneous conditions enclosed within the one or more enclosed areas, according to some examples.
Figure 7:
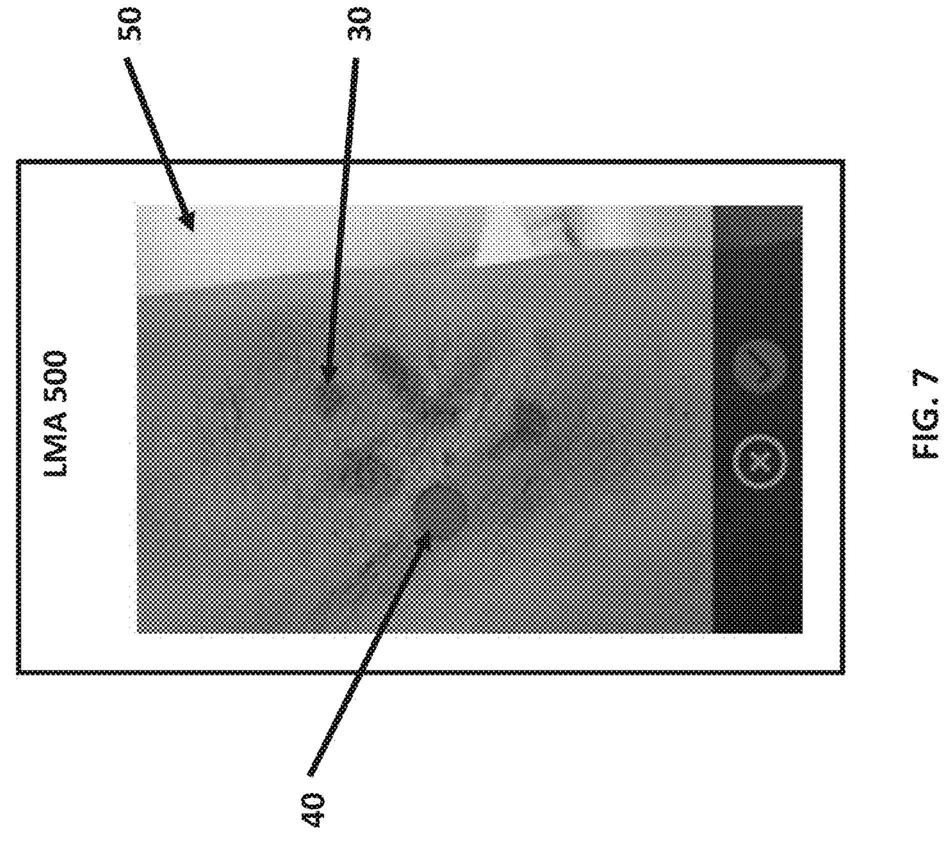
FIG. 7 depicts the captured representation of FIG. 3, according to some examples.
Figure 9:
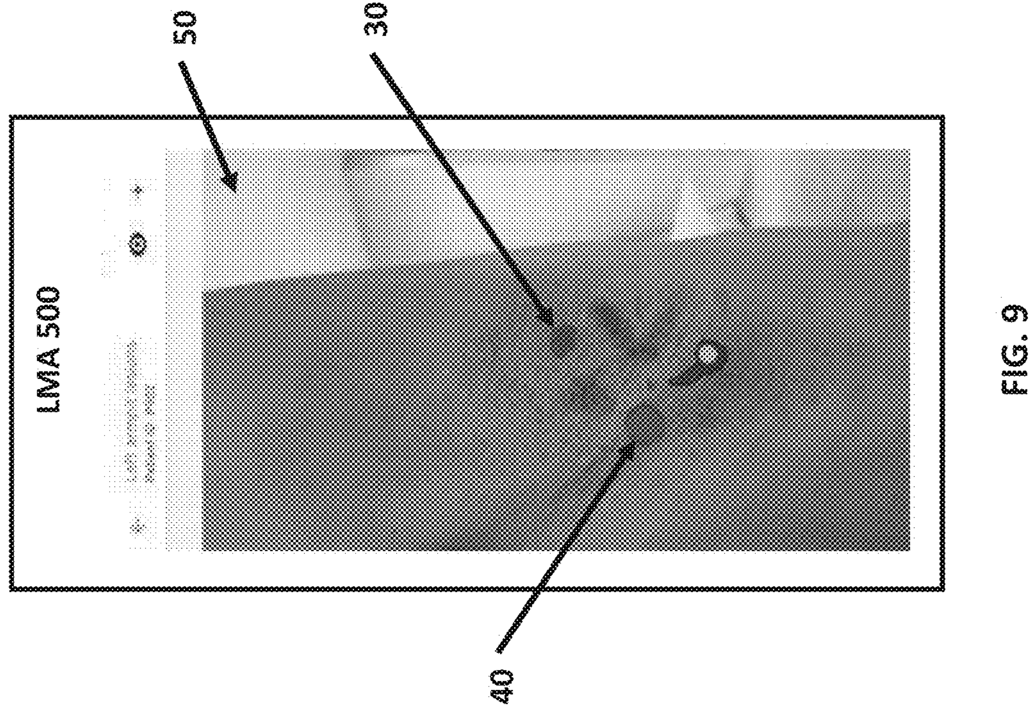
FIGS. 9 and 10 depict the captured representation and the determined characteristics as described in FIG. 6, according to some examples.
Figure 10:
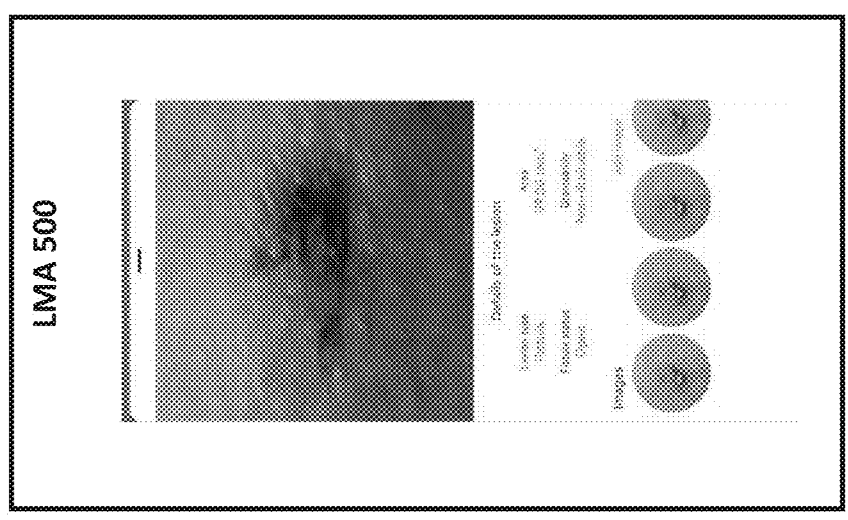

FIG. 6 depicts a flowchart including an example method 400 for rendering, on at least one display, the captured representation and the determined characteristics of the one or more cutaneous conditions enclosed within the one or more enclosed areas. Referring to FIGS. 6, 9, and 10, the method 400 may include a first process 410 of rendering the captured representation on the at least one display. In an illustrative example, the system 500 may render the captured representation 50 on the at least one display 12. The captured representation 50 rendered on the display 12 may include the boundary 60 and the enclosed area 70. In further examples, a user of the system 500 may interact with the display 12 to view any sets of determined characteristics of the cutaneous condition 30 enclosed by the boundary 60.

In another example, the method 400 may include a second process 420 of rendering a visual representation of the third set of characteristics corresponding to the cutaneous condition within the enclosed area on the at least one display. In an illustrative example, the system 500 may render the third set of characteristics corresponding to the cutaneous condition 30. The system 500 may render the third set of characteristics based on user input received, for e.g., by the display 12. In further examples, the system 500 may allow the user to interact with the display 12 to modify any values and/or quantities of the third set of determined characteristics.

In another example, the method 400 may include a third process 430 of rendering a portion of the captured representation on the at least one display, the portion corresponding to the cutaneous condition within the enclosed area. For example, the system 500 may render, on the at least one display, a portion of the captured representation of the cutaneous surface, the portion of the captured representation corresponding to the one or more cutaneous surfaces present on the captured representation. The system 500 may perform this operation based on user input received, for e.g., by the display 12. In an illustrative example, the system 500 may render a portion of the captured representation 50, that corresponds to the cutaneous condition 30.

In another example, the method 400 may include a fourth process 440 of rendering one or more portions of previously captured representations of the cutaneous condition within the enclosed area on the at least one display.

In another example, the method 400 may include a fifth process 450 of rendering one or more visual representations of previously determined sets of characteristics corresponding to the cutaneous condition within the enclosed area on the at least one display.

For example, in allowing the user to access previously determined sets of characteristics corresponding to the one or more cutaneous conditions, the system 500 may render, on the at least one display, portions of previously captured representations corresponding to a cutaneous condition of the one or more cutaneous conditions. The system 500 may render the portions of previously captured representations such that the portions of previously captured representations corresponding to temporally distinct mappings of the cutaneous condition may be rendered simultaneously.

In another example, the first process 410, the second process 420, the third process 430, the fourth process 440, and the fifth process 450 may occur simultaneously, for e.g., during the same evaluation of the cutaneous surface.

FIG. 11 depicts interactive prompts generated by the system 500 according to some examples. Referring to FIG. 11, the system 500 may also generate prompts on a present or later mapping(s) of the cutaneous surface, for the user to update any values and/or quantities including any notes or observations corresponding to the one or more cutaneous conditions of the cutaneous surface to encourage a complete ongoing record of the cutaneous conditions being monitored. In an illustrative example, the system 500 may cause the processor 10 to generate one or more prompts PR corresponding to the determined characteristics of the cutaneous condition 30 on the cutaneous surface 20.

In another example, the system 500 may cause the at least one processor to render, on the at least one display, the one or more prompts generated by the system 500. In an illustrative example, the system 500 may cause the display 12 via the processor 10 to render the one or more prompts PR. A user of the system 500 may input, on the display 12, any values and/or quantities, including any notes or observations in response to the one or more prompts PR. The values and/or quantities inputted by the user in response to the one or more prompts PR may be stored in a central repository, for e.g., stored in cloud database 16, such that the inputted values and/or quantities may be accessed at a later time and/or location.

In another example, the prompts generated by the system 500 on the display may be interactive, such that a user is able to manually interact with the prompts via the display, for e.g., via a capacitive-touch based mechanism of the display. In an illustrative example, the user may interact the display 12 to interact with the one or more prompts PR rendered on the display 12.

In another example, the system 500 may allow a user to interact with the display, such that the user is able to access past assessments, including previously captured representations and previously determined characteristics, of the one or more cutaneous conditions of the cutaneous surface. In an illustrative example and with reference to FIG. 10, the system 500 may allow the user to interact with the display 12 to view information corresponding to previously conducted assessments, including previously captured representations and previously determined characteristics of the cutaneous condition 30. In further examples, the system 500 may allow the user to interact with the display 12 to edit information corresponding to previously conducted assessments, including previously captured representations and previously determined characteristics of the cutaneous condition 30.

In another example, the system 500 may allow a user to interact with the display, such that the user may input information corresponding to the subject whose cutaneous surface is being mapped. For example, the system 500 may allow a user to input information, including the birth date, medical history, and any other applicable information, that corresponds to the subject. The information inputted by the user of the system 500 may be associated with a subject profile, such that any information associated with any and/or all mappings of the subject, including any determined characteristics of the one or more cutaneous conditions of the cutaneous surface of the subject, may be accessed at a later time and/or location.

In another example, the system 500, through the at least one processor, may apportion the total surface area of the cutaneous surface into one or more segments of the cutaneous surface (for e.g., the head, the right arm, the right leg, etc.). In further examples, a user of the system 500, for e.g., a clinician, may interact with the at least one display to select a segment of the one or more segments of the cutaneous surface. for mapping of the one or more cutaneous conditions thereon.

Figure 12:
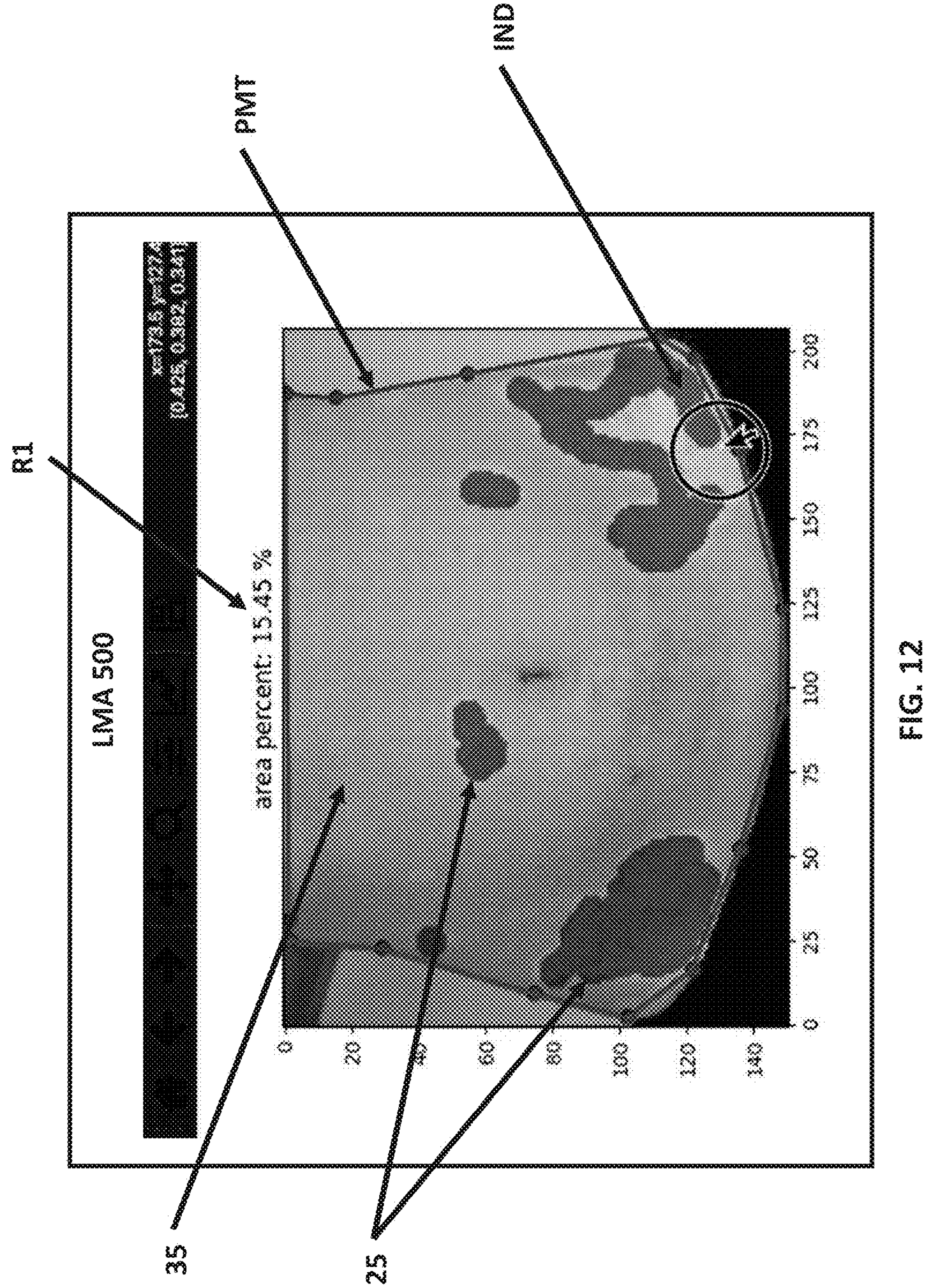
FIG. 12 depicts a ratio generated by the system according to some examples.

In some examples, and with respect to FIG. 12, the system 500 may determine, via the at least one processor, a ratio based on the determined characteristics of the one or more cutaneous conditions and/or the determined characteristics of the one or more measurement markers.

In another example, the ratio determined by the system 500 may be between a first characteristic corresponding to a first portion of the cutaneous surface with respect to a second characteristic corresponding to a second portion of the cutaneous surface. In an illustrative example, the system 500 may determine a ratio R1 between a first characteristic 80 corresponding to a first portion 90 of the cutaneous surface 25 with respect to a second characteristic 85 corresponding to a second portion 95 of the cutaneous surface 25.

In another example, the first characteristic may comprise a qualitative and/or quantitative value that corresponds to the first portion of the cutaneous condition. In further examples, the second characteristic may comprise a qualitative and/or quantitative value that corresponds to the second portion of the cutaneous condition.

In another example, the first portion and/or the second portion may comprise the entirety of the cutaneous surface being evaluated (for e.g., the entirety of the cutaneous surface of the patient being evaluated). In further examples, the first portion and/or the second portion may comprise portion(s) of the cutaneous surface shown in the captured representation.

In another example, the first portion and/or the second portion may comprise portion(s) of the cutaneous surface having the one or more cutaneous conditions. For example, the system 500 may determine a ratio between the total surface area of the portion(s) of the cutaneous surface having the one or more cutaneous conditions with respect to the total surface area of the portion(s) of cutaneous surface shown in the captured representation.

In another example, the first portion and/or the second portion may be defined by the system 500 through Artificial Intelligence/Machine Learning ("AI/ML") algorithm(s), including AI/ML algorithms optimized for image processing, stored in the at least one memory and executed by the at least one processor. For example, the system 500 may form, via the AI/ML algorithm(s), a first perimeter on the captured representation to define the first portion and a second perimeter on the captured representation to define the second portion.

In another example, the first portion and/or the second portion may be defined by the user of the system 500. In some examples, the user of the system 500 may interact with the at least one display to place a perimeter on the captured image to respectively define the first portion and/or the second portion. In an illustrative example, the user of the system 500 may place a perimeter PMT around the cutaneous surface 25 to define the first portion 90.

In other examples, the user of the system 500 may interact with the at least one display to manually define the first portion and/or the second portion of the cutaneous surface. In an illustrative example, the user of the system 500 may use a pointer, for e.g., a finger, on the display 12 to place an indicator IND corresponding to the respective surface areas of the cutaneous conditions 35 to define the second portion 95.

In another example, the first portion, the second portion, and/or a combination of both may be defined by the system 500 and/or based on user input from a user of the system 500. In an illustrative example, the user of the system 500 may place a perimeter PMT around the cutaneous surface 25 to define the first portion 90 and place an indicator IND corresponding to the respective surface areas of the cutaneous conditions 35 to define the second portion 95.

In further examples, the user may modify the first portion and/or the second portion previously defined by the system 500, for e.g., by interacting with the at least one display.

In an illustrative example, a user of the system 500 may define the first portion 90 to comprise the cutaneous surface 25 and the second portion 95 to comprise the cutaneous conditions 35, as depicted in FIG. 12. The user may further define the first characteristic 80 to correspond to the total surface area of the first portion 90 and the second characteristic 85 to correspond to the total surface area of the second portion 95. The system 500 may then contemporaneously determine, via the processor 10, the ratio R1 between the first characteristic 80 of the first portion 90 with respect to the second characteristic 85 of the second portion 95.

In this way, a user of the system 500, such as a clinician, is able to determine the ratio between varying characteristics and/or portions of a patient's cutaneous surface, including a ratio between the total surface area of the patient's cutaneous surface affected by cutaneous conditions with respect to the total surface area of the patient's body unaffected by the cutaneous conditions (or the total surface area of the entirety of the patient's body including the affected portions), to aid in evaluating progression of the cutaneous conditions. Thus, the system 500 allows the clinician to maintain accuracy and consistency in subsequent evaluations of the cutaneous conditions, even if preceding evaluations are conducted by other clinician(s).

In one or more examples, the system 500 may be configured to perform a method, the method comprising: identifying a body map 600; identifying one or more body regions 610 corresponding to the body map 600; identifying one or more captured representations 700 corresponding to the one or more body regions 610; identifying one or more icons 710 corresponding to the one or more captured representations 700; and defining the one or more icons 710 on the one or more captured representations 700.

In one or more examples, the system 500 may be configured to perform a method, the method comprising: identifying a body map 600; identifying one or more body regions 610 corresponding to the body map 600; identifying one or more default representations 800 corresponding to the one or more body regions 610; identifying one or more icons 810 corresponding to the one or more default representations 800; and defining the one or more icons 810 on the one or more default representations 800.

Figure 13:
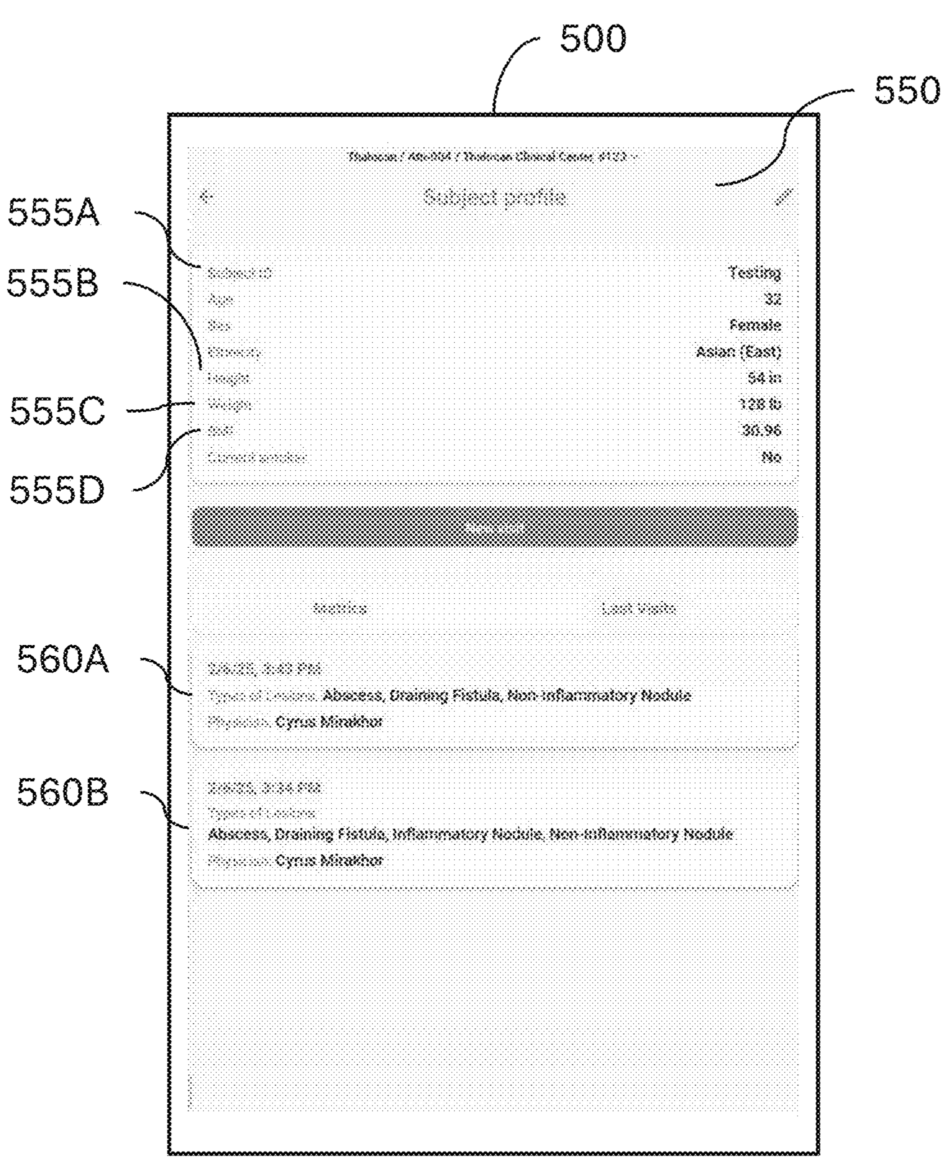
FIG. 13 is an isometric view of a user interface of the system configured to identify a patient profile including one or more patient details and one or more evaluation summaries according to some examples.

FIG. 13 is an isometric view of a user interface of the system 500 configured to identify a patient profile 550 including one or more patient details 555 (e.g., 555A-D) and one or more evaluation summaries 560 (e.g., 560A and 560B), according to some embodiments.

In some examples, the patient profile 550 may include the patient details 555, wherein the patient details 555 represent characteristics of the patient being evaluated, such as at least one of an identification value, age, gender, ethnicity, height, weight, body mass index, smoking preference, consent, or the like. For example, the patient detail 555A may correspond to the identification value, the patient detail 555B may correspond to the height, the patient detail 555C may correspond to the weight, and the patient detail 555D may correspond to the body mass index (BMI), of the patient.

In some examples, the patient details 555 of the patient profile 550, such as the patient details 550A-D, may be identified by the system 500 based on input from the clinician. In this case, upon initializing an evaluation of the patient via the system 500, the clinician may be prompted to input information corresponding to the patient details 555, such as via the display 12, and the system 500 may identify the patient details 555 based on the information inputted by the clinician. For example, the system 500 may prompt the player to input a height and/or weight of the patient to identify the patient details 555B and 555C. The system 500 may further identify the patient detail 555D corresponding to the BMI of the patient, based on the identified patient details 555B and 555C, without the clinician needing to input the BMI of the patient.

In some examples, the patient profile 550 may include one or more evaluation summaries 560, wherein the evaluation summaries 560 provide information corresponding to previous evaluations of the patient. The evaluation summaries 560 may provide information to the date/time that the previous evaluation(s) was performed, the cutaneous conditions of the patient that were evaluated, and the particular clinician(s) that performed the previous evaluations(s). For example, the patient profile 550 may include evaluation summaries 560A and 560B that respectively correspond to a first previous evaluation and a second previous evaluation of the patient. According to the evaluation summary 560A, the first previous evaluation was conducted on "Feb. 6, 2025"at "3:43 PM" by the clinician "Cyrus Mirakhor" of the cutaneous conditions including one or more "abscess, draining fistula, and non-inflammatory nodule" of the patient. According to the evaluation summary 560A, the second previous evaluation was conducted on "Feb. 6, 2025" at "3:34 PM" by the clinician "Cyrus Mirakhor" of the cutaneous conditions including one or more "abscess, draining fistula, inflammatory nodule, and non-inflammatory nodule" of the patient. In this way, the evaluating clinician may quickly and accurately identify which particular cutaneous conditions of the patient have been evaluated before.

Figure 14:
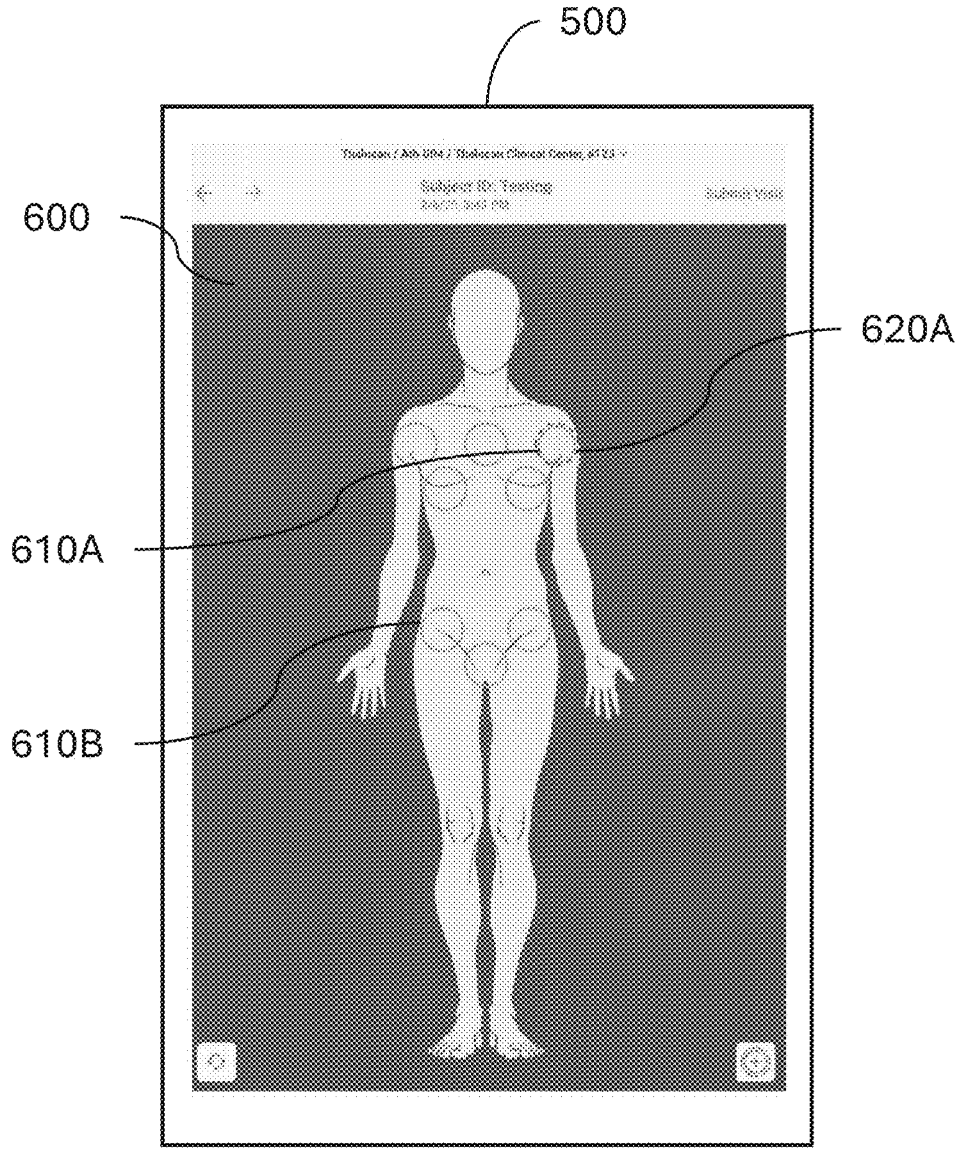
FIG. 14 is an isometric view of a user interface of the system configured to identify a body map including one or more body regions and one or more intervened region indicators, according to some examples.

FIG. 14 is an isometric view of a user interface of the system 500 configured to identify a body map 600 including one or more body regions 610 (e.g. 610A and 610B) and one or more intervened region indicators 620 (e.g., 620A) based on input by the clinician, according to some embodiments.

In some examples, the system 500 may be configured to identify the body map 600 based on the patient profile 550, and render the body map 600 via the display 12.

In some examples, the body map 600 may include a multi-dimensional (e.g., three-dimensional) interactive rendition of the patient, and may include one or more body regions 610, such as body regions 610A and 610B, wherein the body regions 610 represent anatomically separate portions of the patient. For example, the body region 610A may correspond to an underarm area by a left shoulder of the patient, and the body region 610B may correspond to a pubic area by a right hip of the patient. The patient may interact with the displayed body map 600 to change its orientation so that the body regions 610 corresponding to different portions of the patient may be visible. For example, if the portion of the body map 600 being displayed to the clinician corresponds to the front of the patient, the clinician may interact with the body map 600 to change its orientation, to display the portion of the body map 600 that corresponds to the back of the patient.

In some examples, the body regions 610 of the body map 600 may be represented to the clinician by one or more body region indicators rendered by the system 500. For example, the body region 610A may be visually represented by a body region indicator including a circle overlaying the body map 600, corresponding to the underarm area by a left shoulder of the patient. Similarly, the body region 610B may be visually represented by a body region indicator including a circle overlaying the body map 600 and corresponding to the underarm area by a right shoulder of the patient.

In the case that one or more cutaneous conditions of a particular body region have been medically intervened upon, as described further below, the particular body regions may be represented by an intervention indicator 620 (e.g., 620A) rendered by the system 500, in addition to, or in place of, the visual indicators. For example, if the body region 610A has been intervened upon, it may be represented in by the intervention indicator 620A. this way, the intervention indicator may represent that one or more cutaneous conditions of the particular body region have been medically intervened upon in a previous and/or an ongoing evaluation of the patient.

Figure 15:
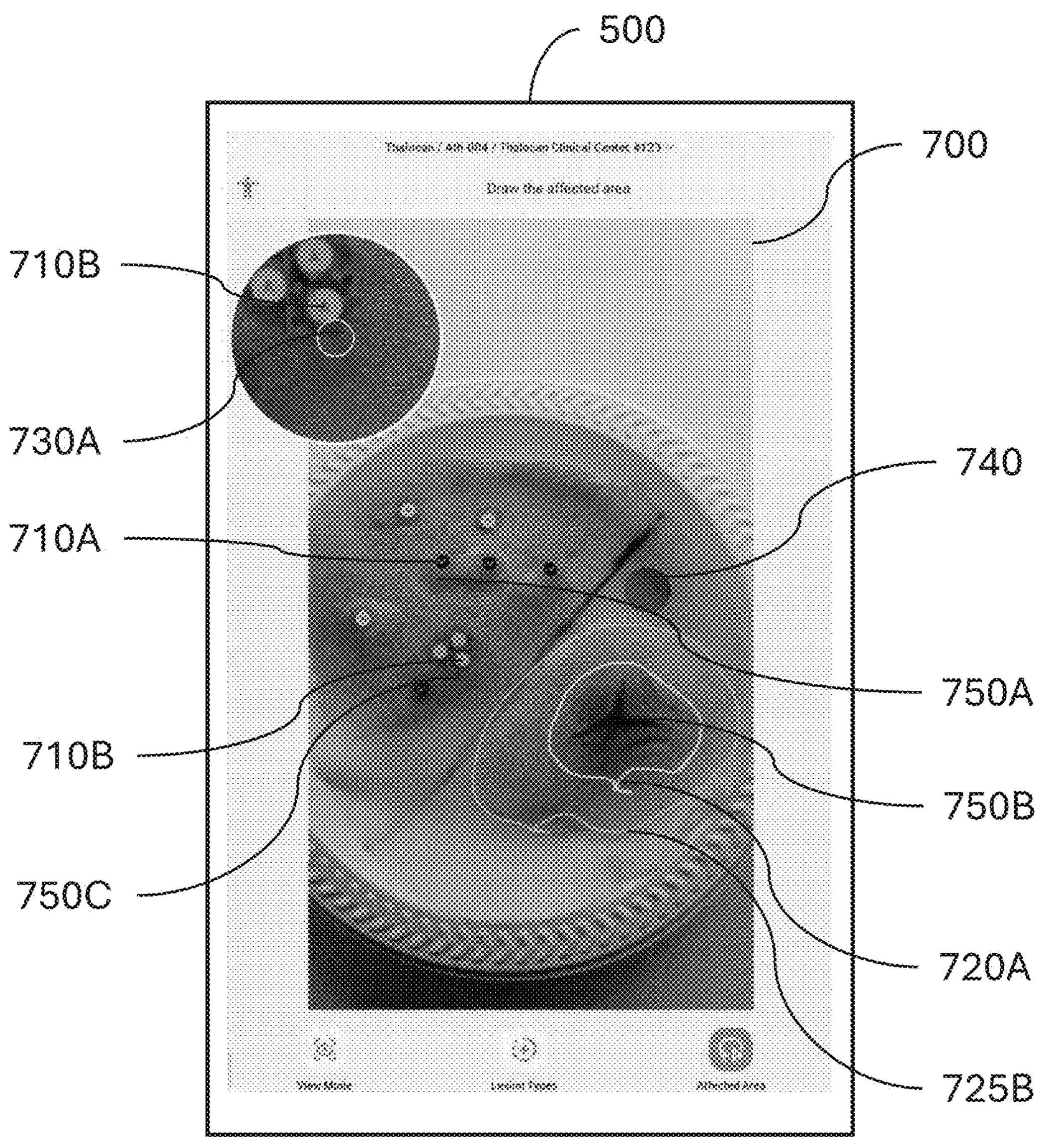
FIG. 15 is an isometric view of a user interface of the system configured to identify one or more captured representations (e.g., captured image) and one or more icons, according to some examples.

FIG. 15 is an isometric view of a user interface of the system 500 configured to identify one or more captured representations, such as captured images 700, corresponding to the one or more body regions 610; identify one or more icons 710 (e.g., 710A and 710B) corresponding to the captured images 700; and define the icons 710 on the captured images 700, according to some embodiments.

In some examples, the system 500 may be configured to identify one or more captured images 700 based on input by the clinician. For example, the system 500 may allow the clinician to select a particular body region, such as via the display 12, to capture the captured image 700. In this case, the system 500 may render a continuous video feed of the selected body region, such as a video feed captured by the camera 11, for displaying to the clinician. The clinician may then interact with the display 12 (e.g., by tapping with a finger and/or stylus) to capture the captured image 700 from the displayed video feed.

Figure 16:
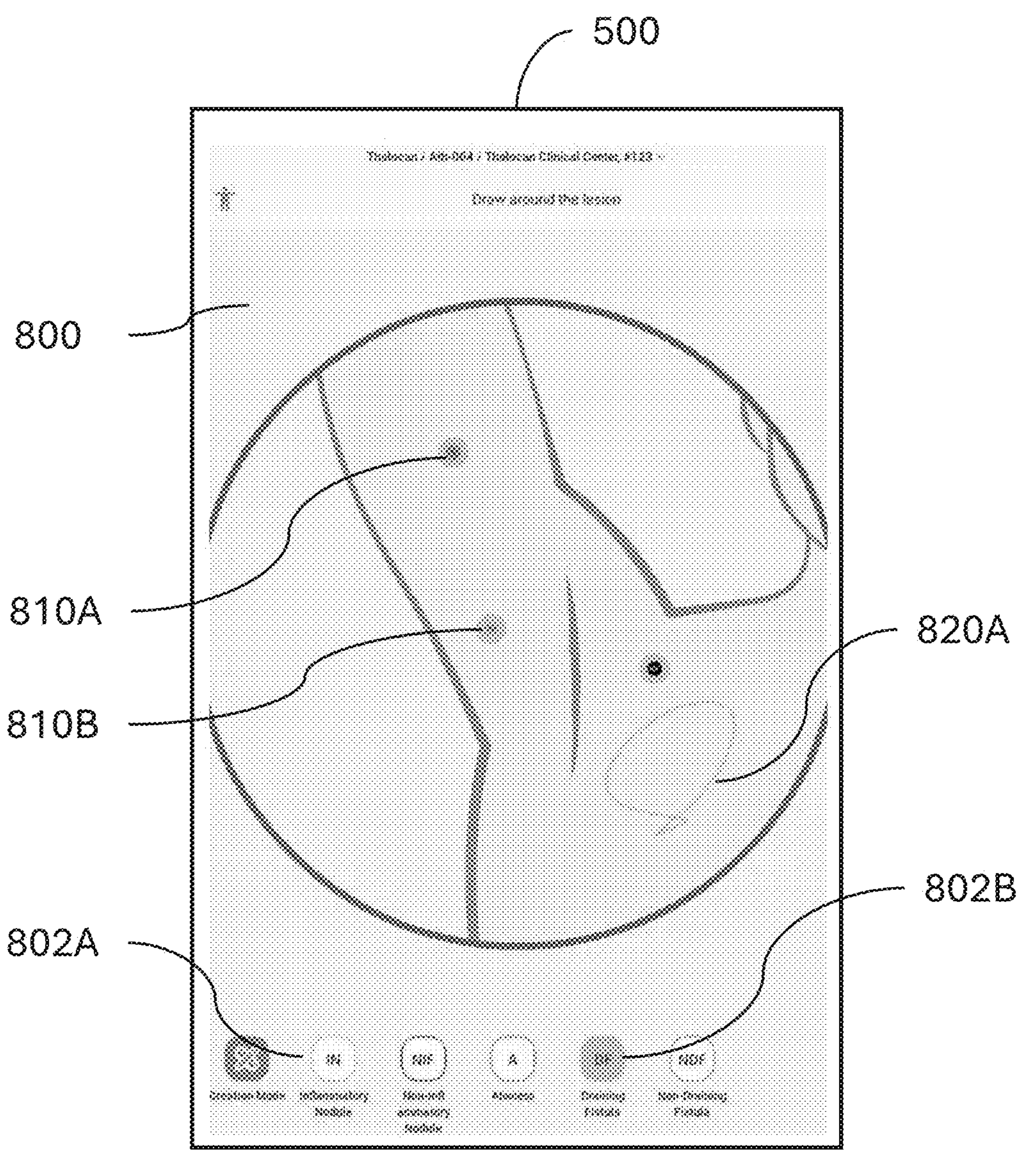
FIG. 16 is an isometric view of a user interface of the system configured to identify one or more default representations (e.g., default image) and one or more icons, according to some examples.

FIG. 16 is an isometric view of a user interface of the system 500 configured to identify one or more default representations, such as one or more default images 800, corresponding to the one or more body regions 610; identify one or more icons 810 (e.g., 810A and 810B) corresponding to the default images 800; and define the icons 810 on the default images 800, according to some embodiments.

In some examples, the system 500 may identify one or more default images 800 based on input by the clinician. For example, the system 500 may present default images 800 of various body sections that can be selected to represent the patient's body parts. The predetermined body image graphics available may have some variation, for male or female patients for example. In this case, upon a particular body region being selected by the clinician, the system 500 may render a default image 800 of the selected body region, in place of the captured image 700. The default image 800 may be predetermined (e.g., generated prior to the evaluation of the patient), and may be retrieved by the system 500 from amongst a plurality of default images stored on a memory (e.g., memory 14) and/or a database (e.g., cloud database 16). Alternatively, the system 500 may have the ability to generate the default image 800 based on an actual patient image (e.g., captured image 700), such as by blurring portions of the actual patient image, and generating the default image 800 based on the blurred portions of the actual patient image. In this way, system 500 allows the clinician to accurately evaluate the selected body region of the patient, while maintaining the privacy of the patient.

In some examples, the system 500 may be configured to identify the default images based on the captured images taken by the clinician. For example, the system 500 may identify the default images based on the particular gender of the subject identified from the captured image. The system 500 may selectively identify the particular default images corresponding to the gender of the subject (e.g., a default image representing gender-specific portions of the body). In this way, the system 500 identifies default images particular to the gender of the subject, thereby allowing for a more accurate evaluation of the cutaneous projections affecting the subject, while maintaining the subject's privacy.

In some examples, the default images may be predetermined (e.g., generated prior to the evaluation of the subject). In this case, the system 500 may be configured to selectively identify the default images from amongst a plurality of predetermined default images that may be stored in a memory and/or database, based on characteristics of the subject being evaluated. The system 500 may provide the default images to the user via the display.

In some examples, the system 500 may identify the default images from amongst the predetermined default images based on the gender of the subject, and render the identified default images on the display In some examples, the system 500 may be configured to include and/or omit physical attributes of the patient's body depicted in the captured images from the default image images that are identified.

In some examples, the system 500 may be configured to allow a user to select a particular default image from amongst the one or more default images identified by the system 500. For example, the system 500 may render the identified default images on the display. The user may then interact with the display, such as via placing a finger on the display, to select the default image corresponding to the portion of the subject having the cutaneous projections, from amongst the default images identified by the system 500. In this way, the clinician may evaluate the particular default image corresponding to the portion of the patient's body having the cutaneous projections.

As used herein, use of the term "representation" without the inclusion of a preceding term may be used to refer to at least one of the one or more captured representations or the one or more default representations, or a combination thereof.

In one or more examples, the system 500 may be further configured to identify one or more icons 710, and define the one or more icons 710 on the captured image 700. The identifying of the one or more icons 710 may include rendering the one or more icons 710 on the display 12, while simultaneously rendering the captured image 700 on the display 12. The clinician may then select a particular icon amongst the displayed icons 710, and place the selected icon onto a portion of the captured image 700 rendered on the display 12. The system 500 may then detect the clinician's selection and placement of the selected icon, and, based on the detection, define the selected icon on the captured image 700.

In some examples, the system 500 may render the icons 710 on a bottom portion of the display 12 (e.g., icons 802 in FIG. 16), and simultaneously render the captured image 700 on a top portion of the display 12. However, the disclosure is not limited thereto, and the icons 710 may be rendered simultaneously with the captured image 700 on any applicable portion of the display 12. The icons 710 may represent cutaneous conditions such as an abscess, a draining fistula, an inflammatory nodule, a non-inflammatory nodule, and/or the like.

In some examples, the icons 710 rendered on the bottom portion of the display 12 may have a visual appearance corresponding to the particular cutaneous condition that the icons 710 respectively correspond to. Referring to FIG. 16, a particular icon 802A may be used to represent an inflammatory nodule, and may thus have a visual appearance, such as a stylized "IN" wherein the "IN" corresponds to the nomenclature of the cutaneous condition, in this case, an inflammatory nodule. However, the disclosure is not limited thereto, and any visual quality indicative of a cutaneous condition may be used to associate an icon with the cutaneous condition that it represents.

In some examples, the clinician may select a particular icon from amongst the icons rendered on the bottom portion of the display 12, for placing onto the captured image 700 rendered on the top portion of the display 12. For example, the clinician may select (e.g., via placing a finger and/or stylus) an icon 710A, corresponding to the cutaneous condition 750A, for placing on the captured image 700.

In this case, the clinician may, after selecting an icon displayed on the bottom portion, place the selected icon onto the top portion of the display 12 depicting the captured image 700. The clinician may place their finger and/or stylus onto the desired portion of the captured image 700, in this case, which depicts the cutaneous condition 750A. The system 500 may detect the selection and placement of the icon 710A by the clinician, and, based on the detection, may define the icon 710A on the portion of the captured image 700 that corresponds to the cutaneous condition 750A.

The clinician may similarly place any of the icons rendered on the bottom portion of the display (e.g., icons 802 shown in FIG. 16) on any portion of the captured image 700 that is rendered on the top portion of the display 12. For example, the clinician may instead select an icon 710B instead of icon 710A, and place the selected icon 710B onto the portion of the captured image 700 representing the cutaneous condition 750B.

In the case that the clinician and/or patient elect to use the default image 800 for evaluation, the system 500 may be configured to allow the clinician to place the icons 810 (e.g., icons 810A and 810B of FIG. 16) on the default image 800 rendered on the top portion of the display 12, to indicate the presence of a cutaneous condition on the default image 800.

In this way, the clinician is able to indicate particular cutaneous conditions that may be depicted on the captured image 700 or the default image 800, by placing the icons 710 or 810 on the particular cutaneous condition(s) depicted by the captured image 700 or the default image 800. This allows for more comprehensive and accurate evaluations of the cutaneous conditions afflicting the patient, even as characteristics of such cutaneous conditions evolve.

Further, patient evaluations of certain cutaneous conditions, such as Hidradenitis suppurativa (HS) may be erroneous across consecutive evaluations, in part because such cutaneous conditions have rapidly evolving characteristics, including a rapidly shifting shape and/or area. Indeed, certain portions of the cutaneous condition may be characterized during an initial evaluation, but may be characterized differently during subsequent evaluations because the cutaneous conditions may progress in an irregular fashion. In such a case, it is desirable to offer the clinician improved methods to evaluate the cutaneous conditions of the patient.

To improve the evaluation of the cutaneous conditions afflicting the patient, the system 500 may be further configured to allow clinicians to place one or more boundaries, such as the first outlines 720A and/or 820B and second outlines 720B and/or 820B on the captured image 700 rendered in a top portion of the display 12. The first outlines 720A and/or 820A may be placed by the clinician around a cutaneous condition. The second outlines 720B and/or 820B may be placed by the clinician around the portion of the patient's skin that is affected by a particular condition.

In some examples, the system 500 may be configured to allow a clinician to place the first outline 720A on the captured image 700 and/or a first outline 820A on the default image 800, wherein the first outline 720A and/or 720*b* correspond to a cutaneous condition depicted on the captured image 700 and/or the default image 800. For example, the system 500 may display the captured image 700 for evaluation, and allow the clinician to select a portion of the captured image 700 representing the cutaneous condition 750B for placing the first outline 720A.

In some examples, to begin placing the first outline 720A, the clinician may click on an icon rendered at the bottom of the display 12, such icon 802B shown in FIG. 16, which corresponds to a draining fistula (DF), which may be common symptom for Hidradenitis suppurativa (HS). The clinician, after selecting the icon 802B, may then trace their finger and/or stylus along the desired portion of the display 12, to place the first outline 720A. The system 500 may detect the placement of the first outline 720A, and based on the detection, may define the first outline 720A on the corresponding portion of the captured image 700, in this case, which depicts a cutaneous condition affected by HS.

In some examples, the system 500 may, based on the clinician's interaction with the captured image 700 (e.g., drawing a boundary around the cutaneous condition 750B), define the first outline 720A on the captured image 700. In the case that the clinician and/or patient elected to evaluate a default image 800, the system 500 may similarly define the first outline 820A based on the clinician's interaction with the default image 800. In this way, the clinician is able to identify and define cutaneous conditions that may have an uneven perimeter, such as a draining fistula, a non-draining fistula, and/or the like.

In some examples, the system 500 may be further configured to allow a clinician to place the second outline 720B, such as a boundary, on the captured image 700 and/or the default image 800. The clinician may place the second outline 720B onto an area affected by a cutaneous condition represented in the captured image 700 and/or the default image 800. For example, the system 500 may allow the clinician to place the second outline 720B onto a portion of the displayed captured image 700 depicting the cutaneous condition 750B. In this case, the system 500 may prompt the clinician to place second outline 720B along the affected area, and the clinician may then trace their finger and/or stylus around the affected area.

The system 500 may detect the placement of the second outline 720B, and, based on the detection, define the second outline 720B on the captured image 700. The clinician may thus, in addition to placing a first outline 720A corresponding to the cutaneous condition 750B, further place a second outline 720B corresponding to the portion of the patient's body that is affected by the cutaneous condition 750B.

In this way, the clinician may analyze a particular cutaneous condition and the area afflicted by the particular cutaneous condition with greater comprehensiveness and accuracy via the system 500. In particular, the system 500 may allow the clinician to place first outlines and/or second outlines to track cutaneous conditions that may have irregular characteristics, including, but not limited to, Hidradenitis Suppurativa (HS), Methicillin-resistant Staphylococcus aureus (MRSA) Inverse Psoriasis (IP), Acne Conglobata (AC), and/or the like.

However, the disclosure is not limited thereto, and the placement of first outlines, such as the first outline 720A and/or second outlines, such as the second outline 720B, may be used to comprehensively evaluate characteristics of cutaneous conditions afflicted by not only HS, but any applicable conditions. For example, the system 500 may be further configured to allow the clinician to place the first outline 720A and/or the second outline 720B on cutaneous conditions depicted in the captured image 700 and/or default image 800 that may be afflicted by Methicillin-resistant Staphylococcus aureus (MRSA), the pathology of which includes irregularly-shaped lesions. The system may be used with a wide variety of skin conditions including, but not limited to, those noted above. For further example, it might be used with Pyoderma gangrenosum (PG), Alopecia, or Vitiligo as well as other skin conditions.

In some examples, the system 500 may be configured to allow a clinician to interact with the captured image 700 and/or the default image 800 rendered via the display 12. For example, the clinician may interact with the display 12, such as by gesturing with their fingers, to enlarge and/or condense the captured image 700 and/or the default image 800, and move the enlarged and/or condensed portions so that different portions are rendered on the display 12. For example, the clinician may place one or more fingers on the display 12 to interact with the displayed captured image 700 and/or the default image 800, to select particular portions thereof to be enlarged. The system 500 may detect the placement of the clinician's fingers to enlarge portions of the captured image 700 and/or the default image 800. The system 500 may then render an enlarged view of the detected portions of the captured image 700 and/or the default image 800 on the display 12. The system 500 may further allow the clinician to move the displayed default image in an enlarged view (e.g., in a vertical direction and/or a horizontal direction), so that different portions of the captured image 700 and/or the default image 800 are visible on the display 12.

Figure 17:
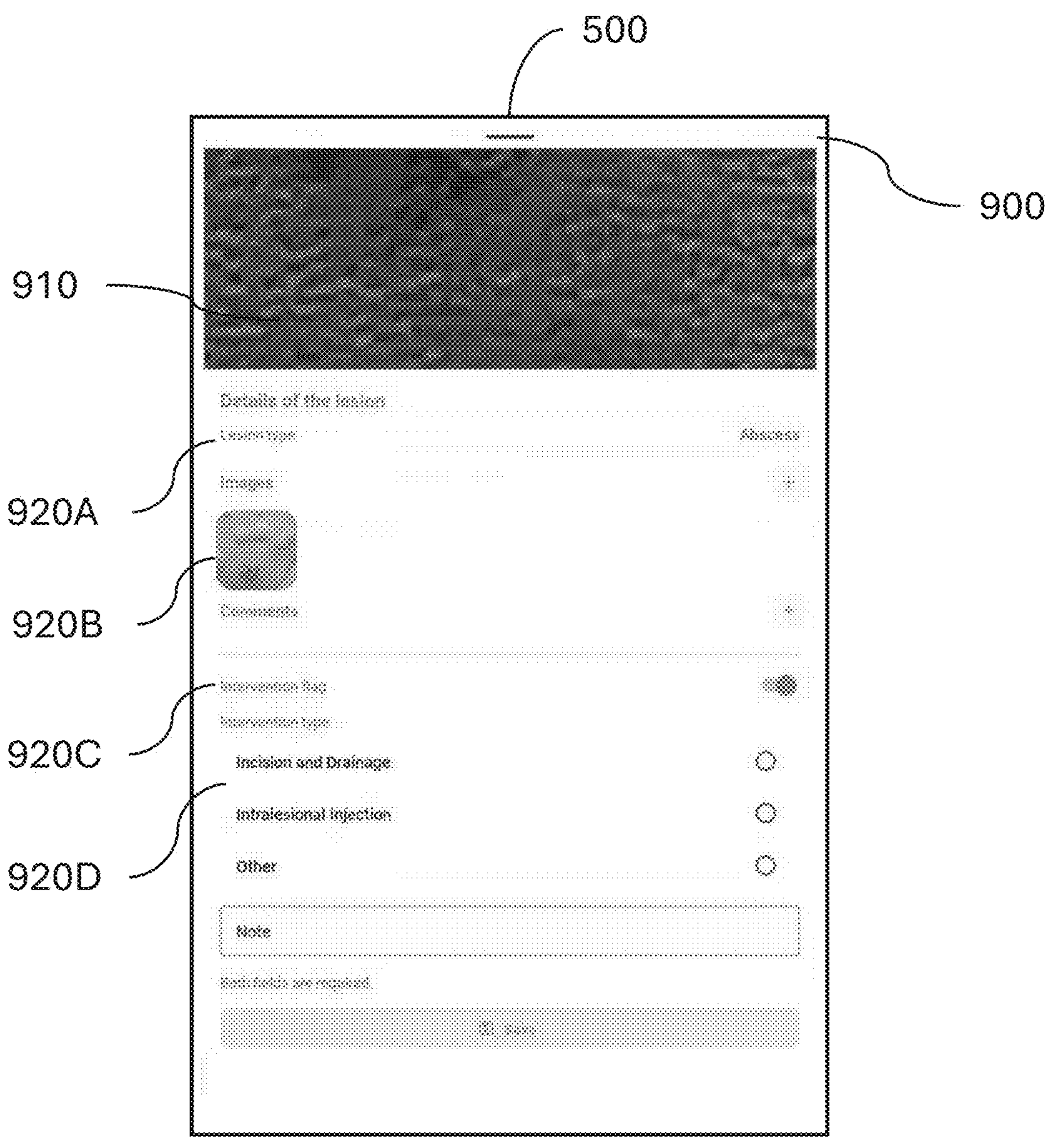
FIG. 17 is an isometric view of a user interface of the system configured to identify a details panel including an evaluation image and one or more evaluation details, according to some examples.

FIG. 17 is an isometric view of a user interface of the system 500 configured to identify a details panel 900 including an evaluation image 910 and one or more evaluation details 920 (e.g., 920A-D), according to some embodiments.

In some examples, the system 500 may be configured to render a details panel 900 corresponding to a particular cutaneous condition of the captured image 700 and/or the default image 800. For example, the clinician may interact with (e.g., pressing with a finger and/or stylus) the icons 710A or 710B defined on the captured image 700, or the icons 810A or 810B defined on the default image 800, to cause the system 500 to render the corresponding details panel, such as the details panel 900. In other examples, the clinician may interact with at least one of a first outline 720A or a second outline 720B defined on a particular cutaneous condition of the captured image 700 to cause the system 500 to render a details panel corresponding to the particular cutaneous condition corresponding to the first outline 720A and the second outline 720B.

In some examples, the details panel 900 may an include one or more evaluation images 910 of the corresponding cutaneous condition. For example, upon selecting an icon from amongst the icons 710A and/or 710B, the system 500 may prompt the clinician to capture an evaluation image 910 of the corresponding cutaneous condition, for addition to the details panel 900.

In some examples, the details panel 900 may further include evaluation details 920 corresponding to cutaneous condition information, an intervention presence indicator, an intervention type indicator, an area indicator, prior evaluation images, evaluation comments, and/or the like.

For example, the evaluation detail 920A may include information identifying the type of cutaneous condition that is being evaluated. The evaluation detail 920B may include selectable thumbnails of previous evaluation images that may have been captured during prior evaluations of the patient. The evaluation detail 920C may include information identifying whether an intervention has been performed on the particular cutaneous condition. The evaluation detail 920D may include information identifying the type of intervention that may have been performed on the particular cutaneous condition, such as an incision and drainage, an intralesional injection, and/or the like. The details panel 900 may further include an area indicator indicating the total area of the patient's body that is directly and/or indirectly affected by the particular cutaneous condition being evaluated.

In some examples, the system 500 may be configured to allow a clinician to modify the evaluation image 910 and/or the evaluation details 920 of the details panel 900. For example, the clinician may add one or more evaluation images 910 to the details panel by selecting a portion of the details panel 900, and capturing one or more evaluation images 910 of the particular cutaneous condition for addition to the details panel 900. The clinician may further remove an evaluation image from the details panel 900 by selecting the particular evaluation image 910 to be removed from the details panel 900.

The system 500 may further allow the clinician to select any of the evaluation details 920 for modification. For example, the evaluation detail 920C of the details panel 900 may include a selectable toggle that allows the clinician to identify whether a lesion has been intervened upon. The evaluation detail 920D may include selectable option that the clinician may select to identify the type of intervention being performed, and may be configured to allow the user to input notes related to the intervention being informed. In this way, the clinician is allowed to track the progression of the cutaneous condition(s) being evaluated.

In the case that the patient being evaluated is medically intervened upon, that is, has undergone medical treatment outside of the course of evaluation, the evaluating clinician may indicate that a medical intervention has been performed on a particular cutaneous condition depicted in the captured image 700 and/or default image 800, and input information corresponding to the medical intervention, by interacting with the evaluation details 920 (e.g. evaluation details 920D). For example, referring to FIG. 15, in the case that the cutaneous condition 750C depicted in the captured image 700 is medically intervened upon, the clinician may first select the icon 710B placed on the cutaneous condition 750C, which may cause the system 500 to render a details panel (e.g., details panel 900 shown in FIG. 17). The clinician may then interact with the evaluation detail 920D of the details panel 900 (e.g., the intervention presence indicator) to indicate the performance of a medical intervention on the cutaneous condition 750C.

The clinician may further interact with the evaluation detail 920D (e.g., intervention type indicator) to indicate information associated with the medical intervention, for example, the type of medical intervention that was performed on cutaneous condition 750C. However, the disclosure is not limited thereto, and the clinician may input any information corresponding to the medically intervention being performed, within the details panel 900. In this way, information associated with medical interventions that are previously performed may be accessed during subsequent evaluations, providing comprehensive tracking of any medical interventions performed on the patient.

Once the evaluating clinician has indicated, such as by way of interacting with the evaluation details 920, that an intervention has been performed on the cutaneous condition 750C, the system 500 may update the visual appearance of the corresponding icon 710B. For example, the system 500 may update the visual appearance of the corresponding icon 710B to include a broken line forming an enclosed circle around the icon 710B, which indicates that the cutaneous condition 750C has been medically intervened upon. Similarly, the system 500 may update the visual appearance of the first outline 720A if the corresponding cutaneous condition 750B is indicated as being medically intervened upon. In this case, the system 500 may update the visual appearance of the first outline 720A as including a broken line corresponding to the edges of the cutaneous condition 750B.

The system 500 may further update the body map 600 so that the body region 610A having the cutaneous condition 750B and/or 750C thereon may be indicated as being medically intervened upon (e.g., via the intervention indicator 620A). For example, as shown in FIG. 14, when the cutaneous condition 750B and/or 750C of the body region 610A is indicated by the clinician to be intervened upon, the body region 610A is depicted on the body map 600 via the intervention indicator 620A, which includes a broken line forming an enclosed circle. Body region 610B, which may not have been medically intervened upon, may not be depicted on the body map 600 using such visual indicators, and is instead represented by a continuous line forming an enclosed circle.

In subsequent evaluations, when the system 500 generates a new body map corresponding to a subsequent evaluation, a particular body region of the body map may visually indicate that one or more cutaneous conditions corresponding to the particular body region has been medically intervened upon, such as by a broken line forming an enclosed circle around the intervened body region. When the system 500 displays the captured image and/or default image corresponding to the cutaneous conditions of the intervened body region, the captured image and/or default image may include one or more icons and/or first outlines that may have been placed and/or defined during previous evaluations. The particular icon(s) corresponding to the cutaneous conditions that have been medically intervened upon may be visually indicated by the system 500. For example, the system 500 may render a broken line forming an enclosed circle around each of the particular icons corresponding to the intervened cutaneous conditions, and may render a broken line surrounding the edges of the intervened cutaneous conditions corresponding to the particular first outlines. In this way, clinician(s) performing subsequent evaluations of the patient may visually discern the body regions and cutaneous conditions that have been medically intervened upon during prior evaluations.

In some examples, the system 500 may be further configured to prevent an evaluating clinician from ending the evaluation if the clinician fails to place an icon or a first outline on a cutaneous condition that has been medically intervened upon. For example, if the evaluating clinician selects a body region to evaluate, but fails to place any icons or first outlines on a cutaneous condition that was previously indicated to have been medically intervened upon, the system 500 may prompt the clinician to place an icon and/or a first outline on the particular cutaneous condition. However, the disclosure is not limited thereto, and the system 500 may employ any methods to prevent the evaluating clinician from ending the evaluation prior to the evaluation of all cutaneous conditions that have been medically intervened upon.

Figure 18:
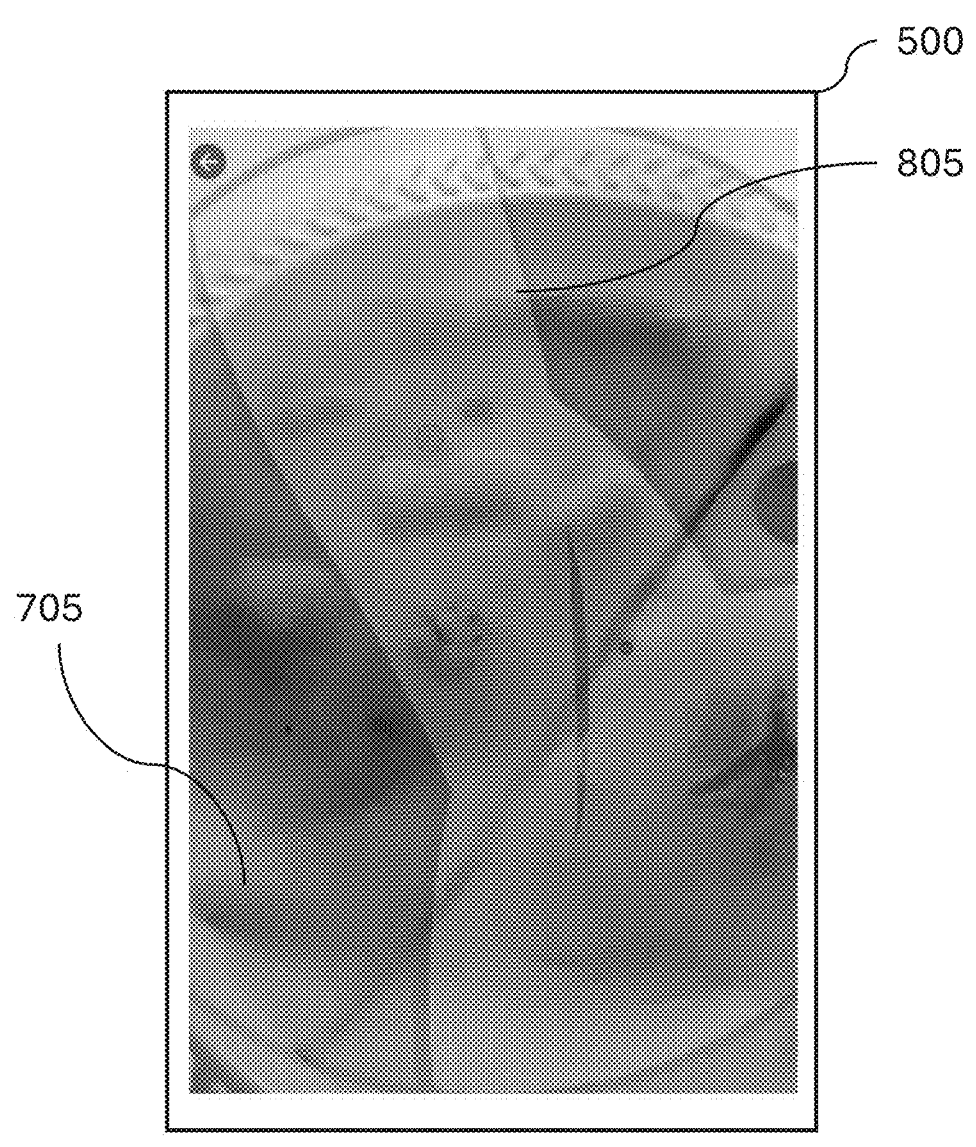
FIG. 18 is an isometric view of a user interface of the system configured to render a ghost representation, according to some examples.

FIG. 18 is an isometric view of a user interface of the system 500 configured to render a ghost representation 805 contemporaneously with a video feed 705 to identify the captured image 700, according to some embodiments.

In one or more examples, the system 500 may be configured to render a ghost image corresponding to a captured image and/or the default image of a prior evaluation of the patient. For example, the clinician may initialize an evaluation of the patient via the system 500, and may select a body region 610 to capture a captured image thereof. The system 500 may then prompt the clinician to capture the captured image 700 by rendering a video feed 705 of the selected body region 610, via a camera of the system 500. The system 500 may further render a ghost image 805 that is superimposed with the video feed 705, for example, by overlaying the ghost image 805 on the video feed 705. The ghost image 805 may correspond to a default image and/or captured image corresponding to a prior evaluation, and in FIG. 18, corresponds to the default image 800. In this way, the ghost image 805 provides a reference for the clinician to capture the captured image of the selected body region, and allows for a consistent evaluation of the cutaneous conditions of a patient, even across multiple sessions of evaluation. The ghost image 805 may include any icons, first outlines, and/or second outlines placed on the captured image and/or default image corresponding to a previous evaluation, which in this case, are icons, first outlines and/or second outlines placed on the captured image 800. The clinician may use the ghost image depicting the previously placed icons, first outlines, and/or second outlines as for reference when capturing a subsequent captured image. Thus, the system 500 may superimpose the ghost image over the video feed in such a way that the skin conditions can be accurately mapped onto the default image and/or captured image, and that is reproducible from one examination to the next.

In some examples, the system 500 may render the ghost image 805 during the clinician's evaluation of the captured image 700, for example, based on a detection that the clinician has selected to view the ghost image 805. For example, the clinician may select a portion of the display 12 to view the ghost image 805 during evaluation of a subsequently captured image. In this way, the clinician, may thus reference the previously placed icons, first outlines, and/or second outlines shown in the ghost image 805, while placing icons, first outlines, and/or second outlines on the subsequently captured image, thereby improving accuracy and consistency across multiple evaluations.

Figure 19:
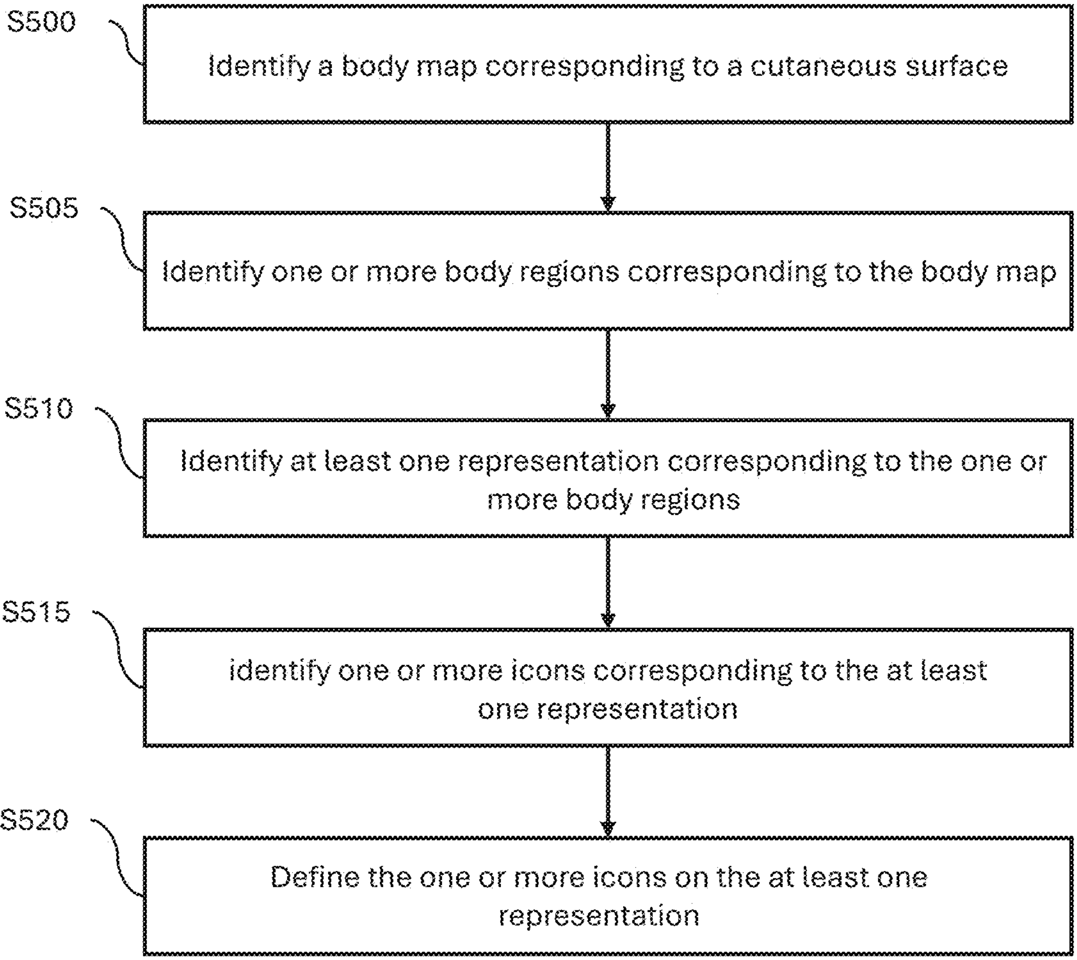
FIG. 19 illustrates a method for evaluating a cutaneous condition, according to some examples.
Figure 20:
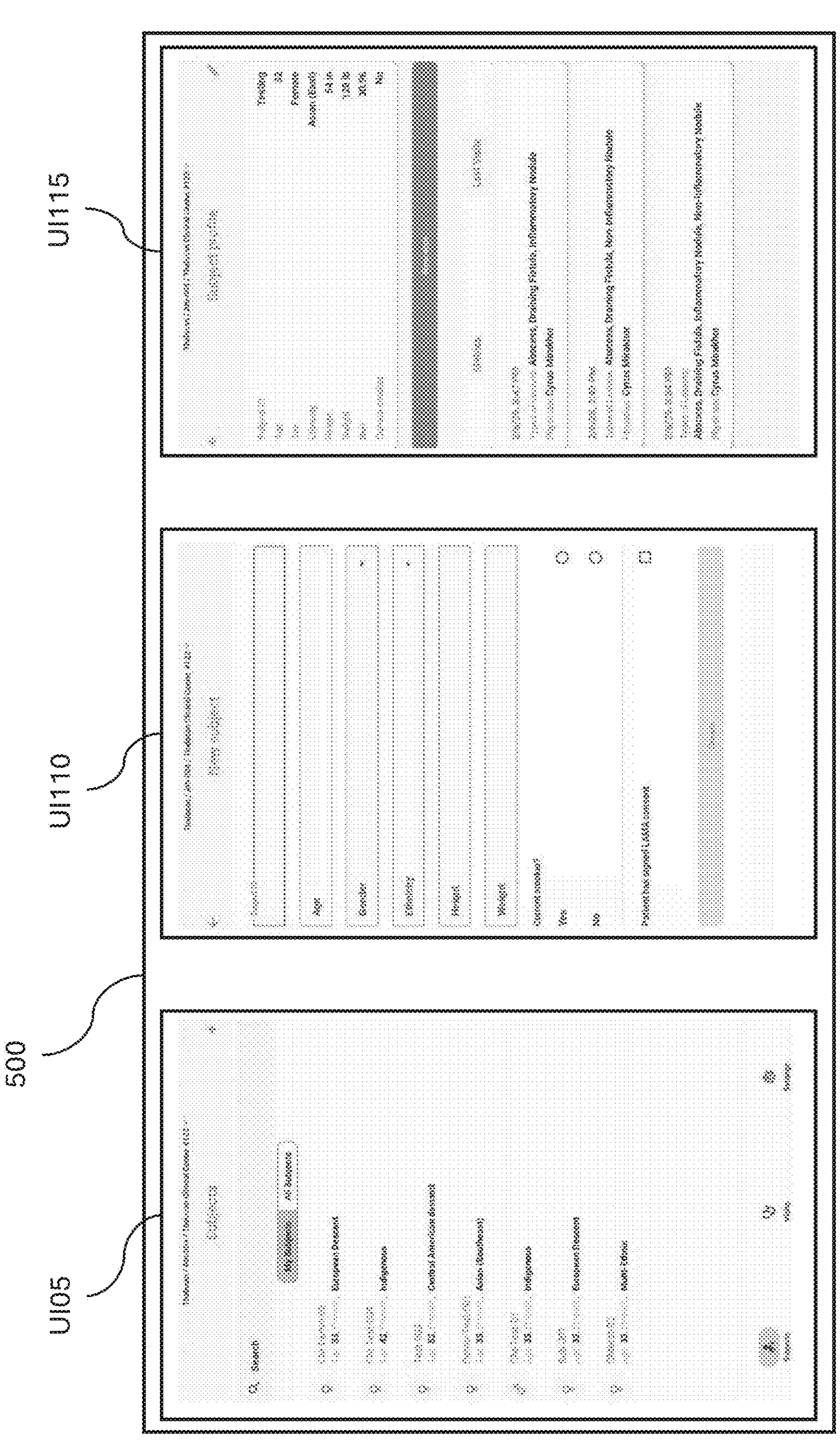
FIGS. 20-27 illustrate various user interfaces of the system, according to some examples.
Figure 21:
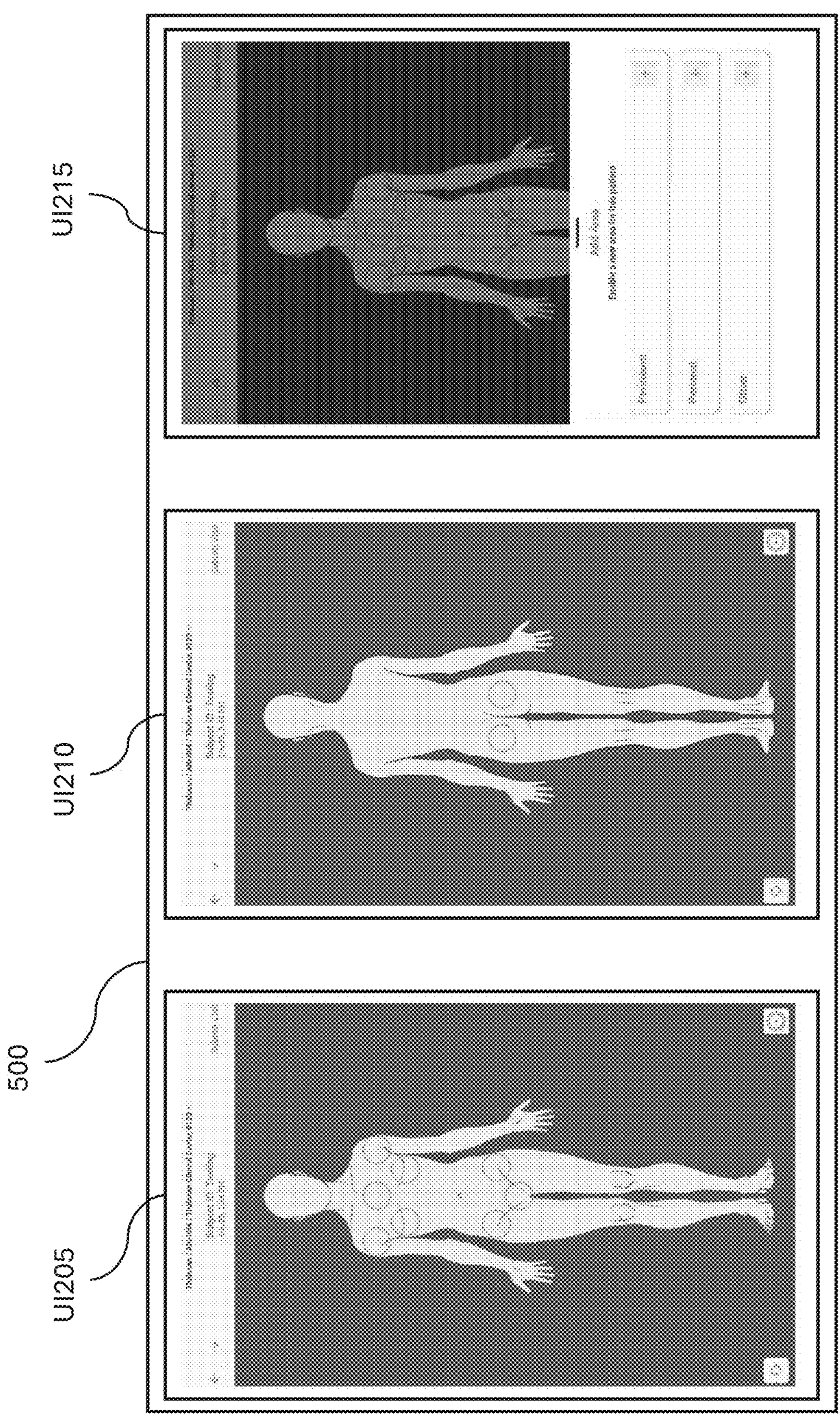
Figure 22:
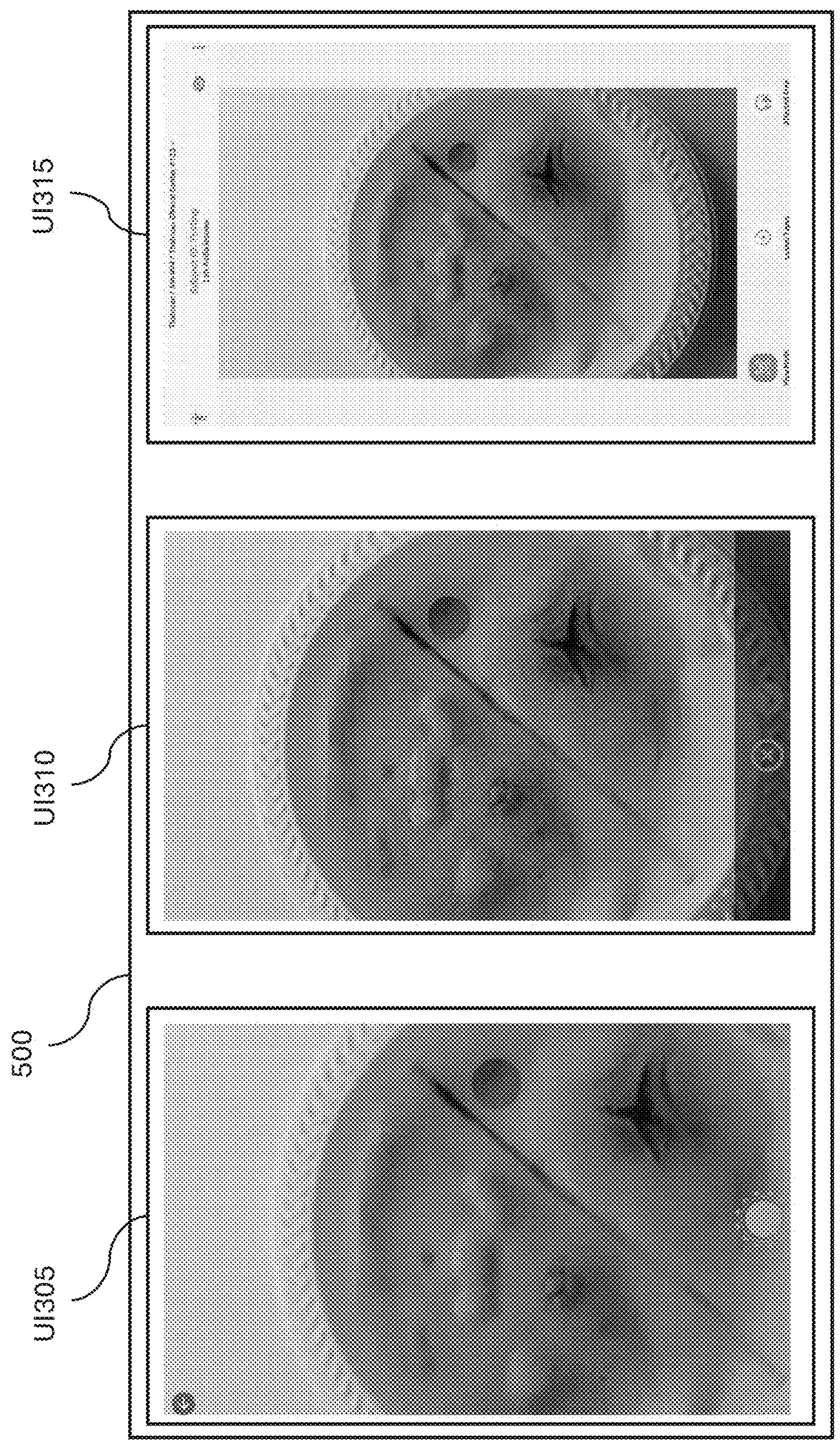
Figure 23:
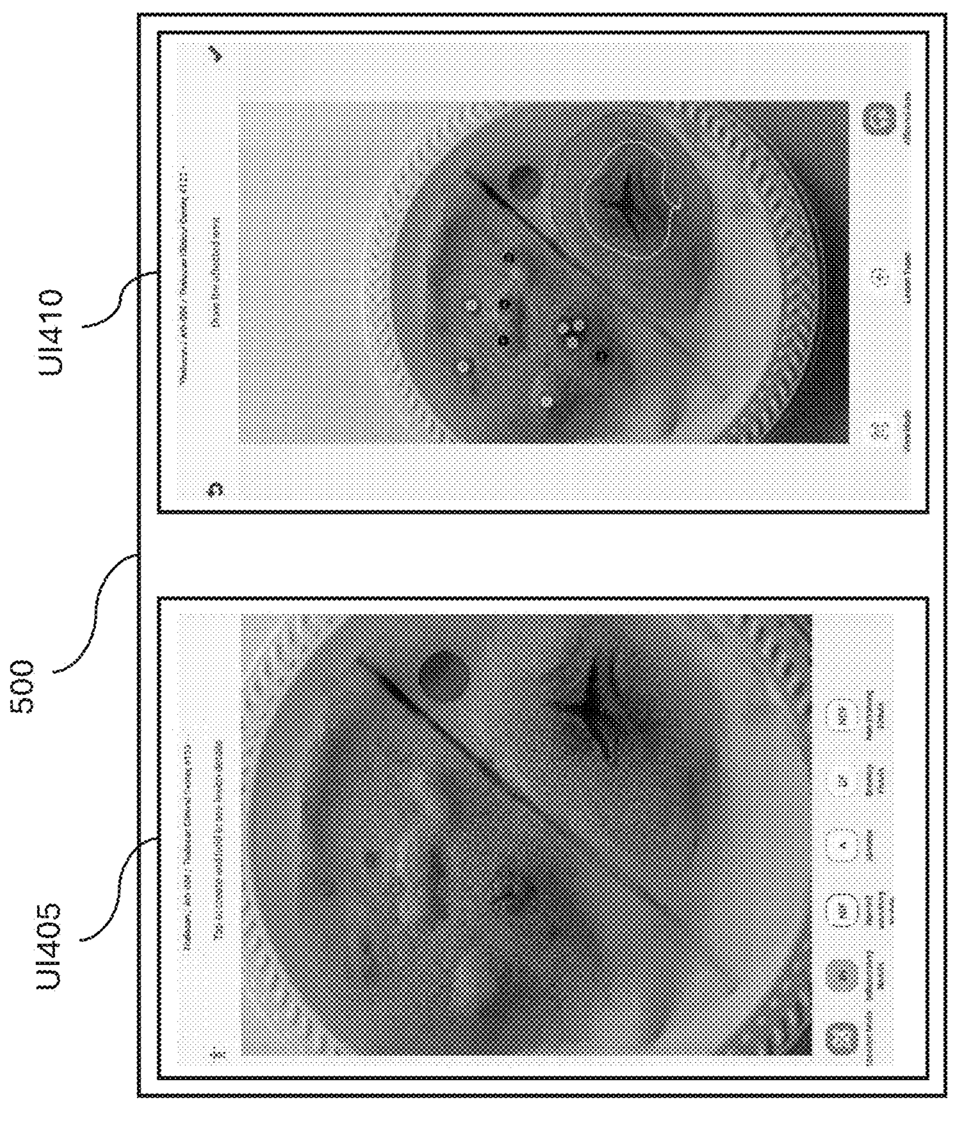
Figure 24:
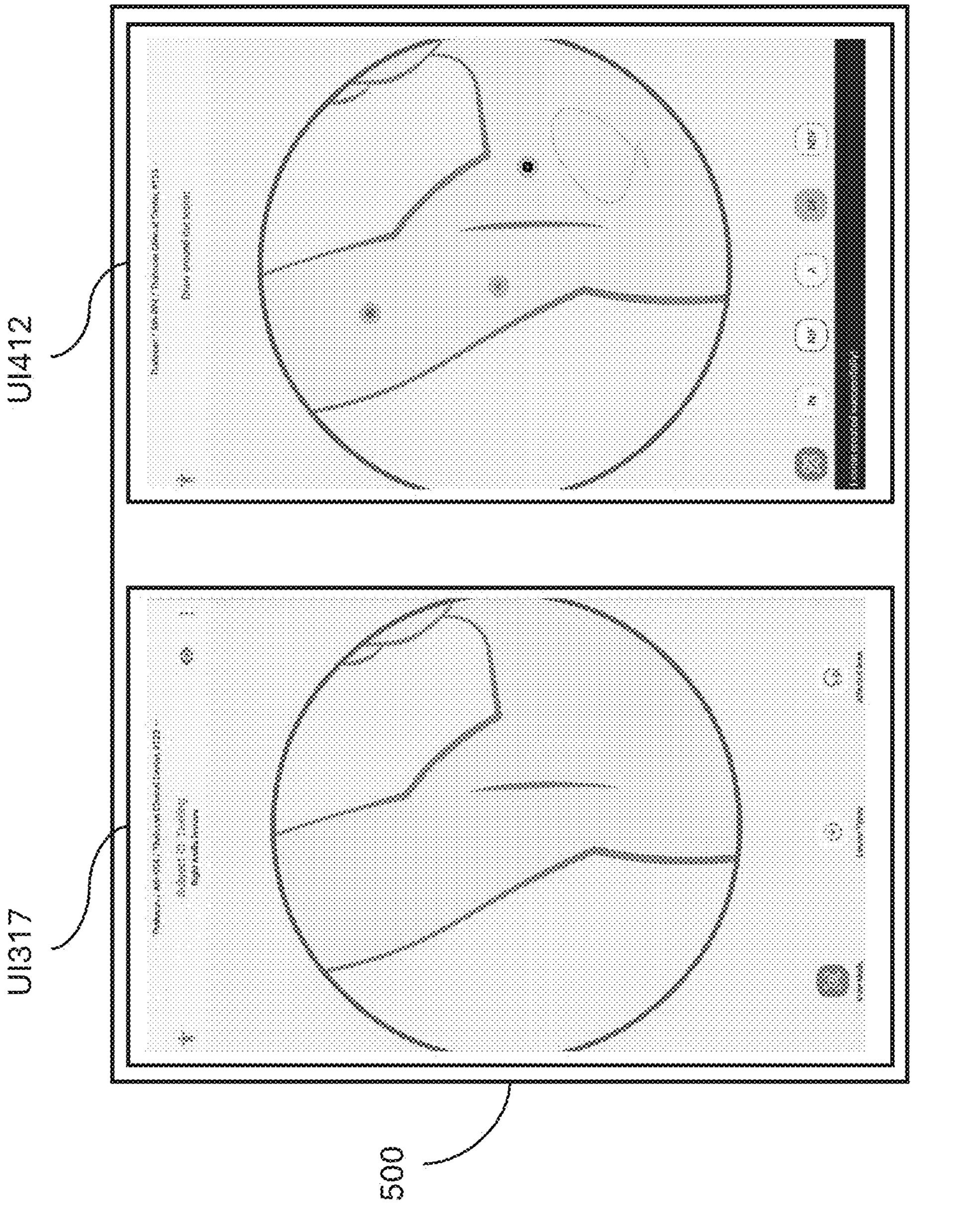
Figure 25:
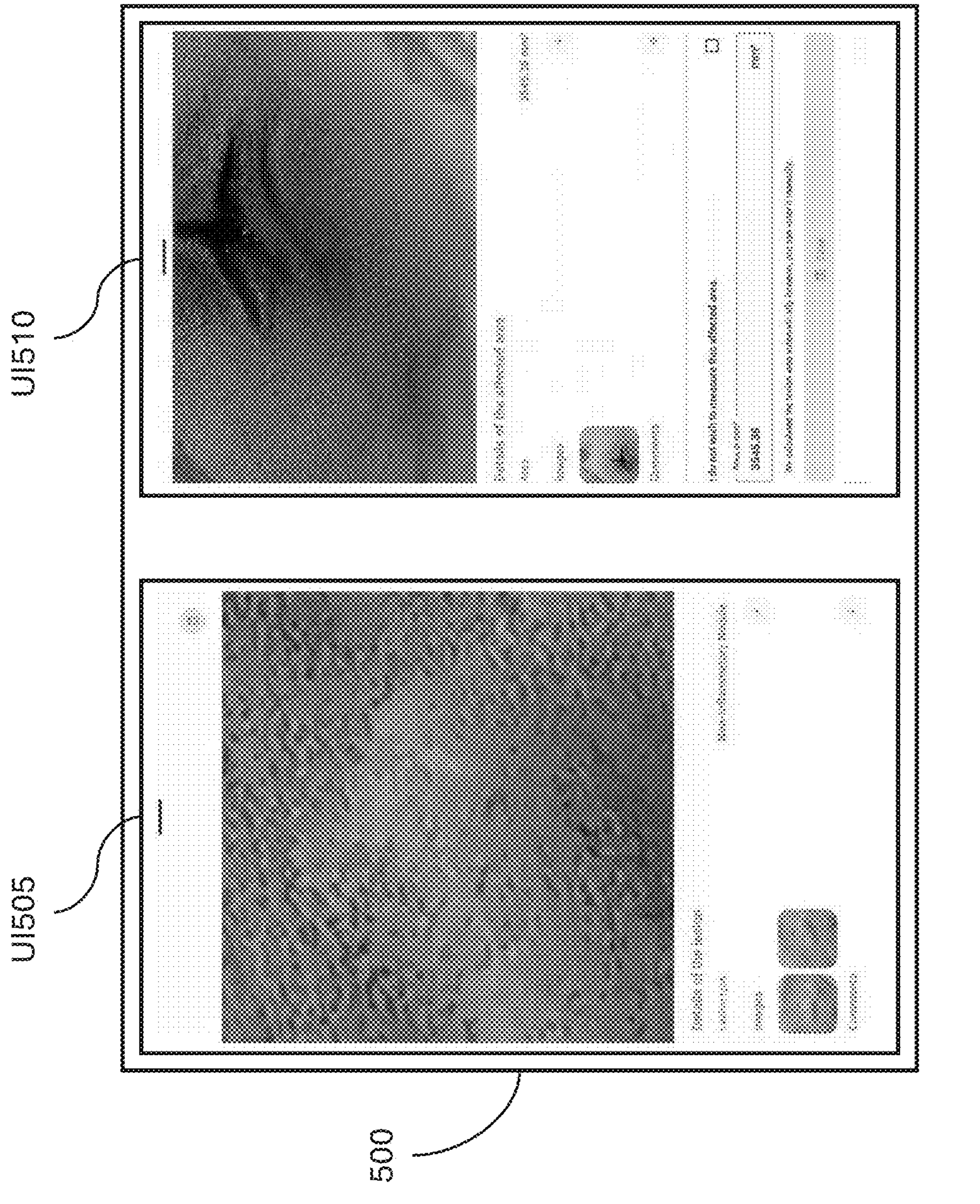
Figure 26:
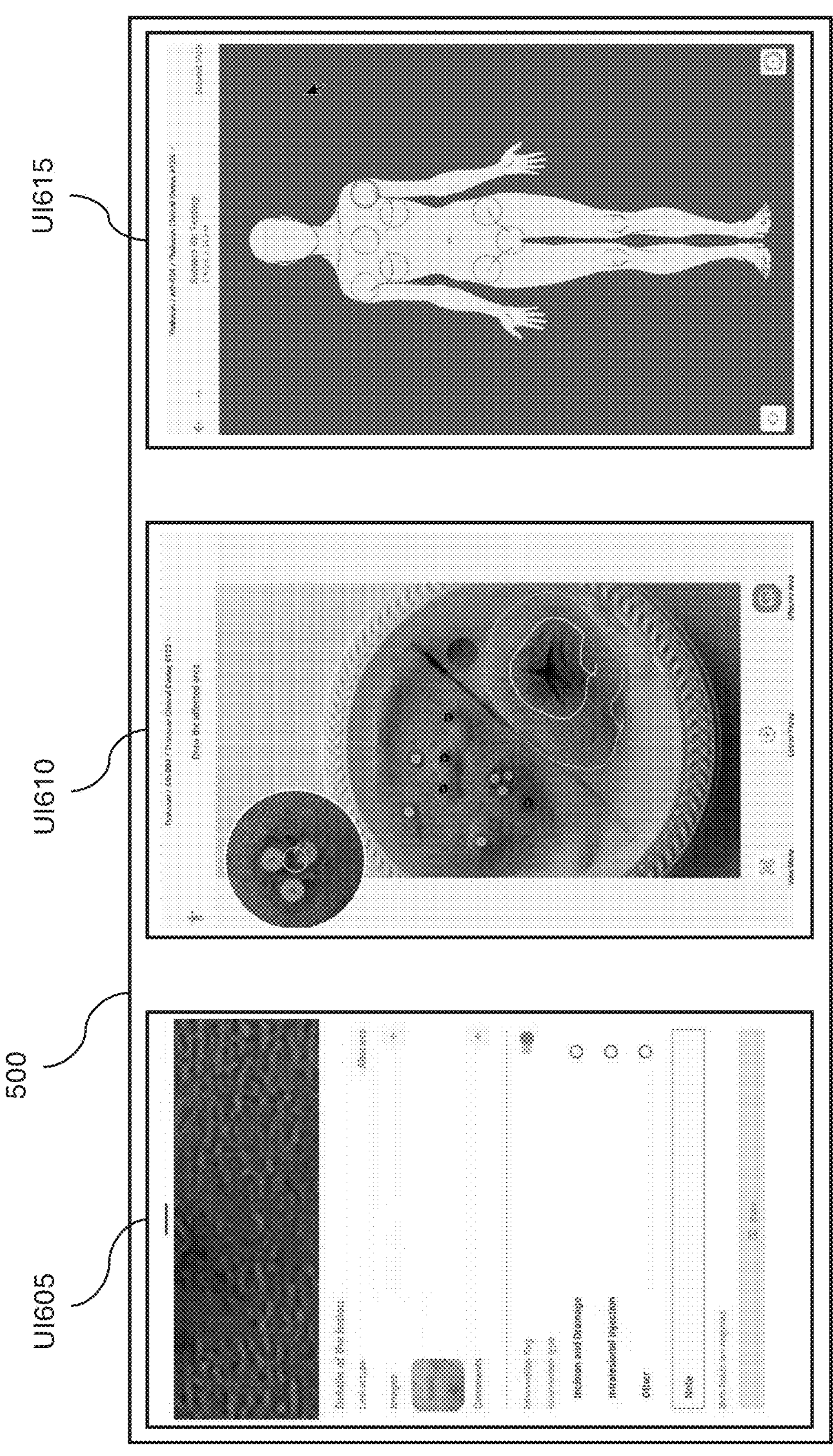
Figure 27:
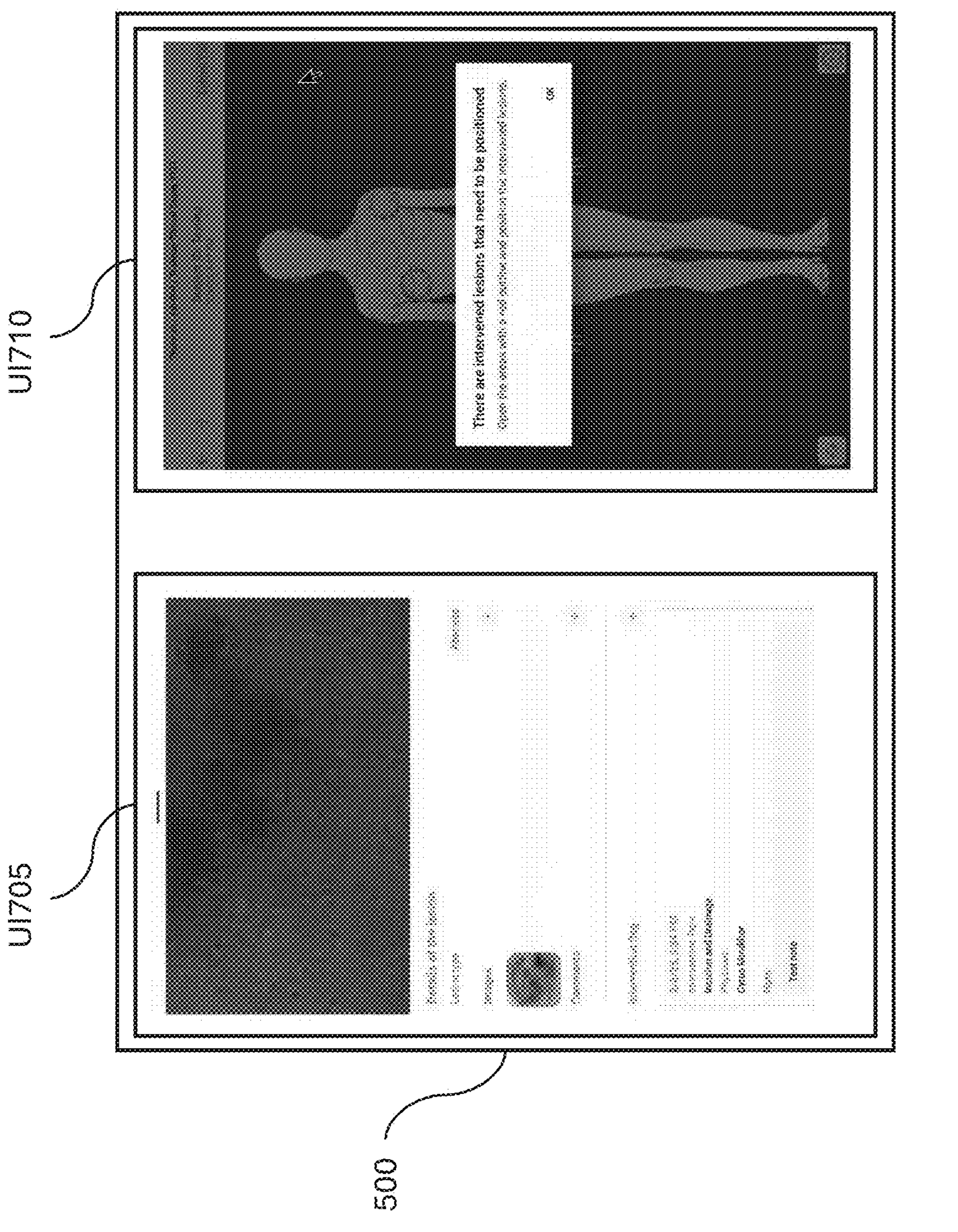

FIG. 19 illustrates a method for evaluating a cutaneous condition, according to some embodiments.

FIGS. 20-27 illustrate various user interfaces (UI) of the system 500.

In some examples, the identifying of the body map (S500) may include identifying a patient profile corresponding to the patient. In this case, the system 500 identifies a patient profile by receiving input from the clinician, for example via UI105, UI110, and UI115 of FIG. 20 rendered on the display 12.

As depicted in UI105, the system 500 may display information corresponding to separate patients that may have been previously evaluated, to the clinician. The system 500 may further allow the clinician to select a particular patient from amongst the displayed patients.

As depicted in UI110, based on the selection of the clinician, the system 500 may request information corresponding to the particular patient selected by the clinician. The system 500 may further allow the clinician to input the requested information on the text boxes rendered on the display 12. Once the clinician has inputted the requested information, they may select a portion of the screen to cause the system 500 to generate the patient profile. As depicted in UI115, the system 500 may generate the patient profile corresponding to the patient, based on the requested information inputted by the clinician, render the generated patient profile on the display 12.

In some examples, the identifying of the body map (S500) may include generating a body map based on the patient profile. The system 500 may generate the body map and render the generated body map on the display 12 for displaying to the clinician, as depicted in UI205, UI210, and UI215 of FIG. 21. As depicted in UI205, the system 500 may identify the body map and corresponding body regions (S505), and display the generated body map having the body regions to the clinician. The system 500 allows the clinician to manipulate the body map so as to view each side of the body, such as the front of the body map depicted in U205, and the back map of the body depicted in UI210. As shown in UI215, the system 500 may further allow the clinician to add additional body regions to the body map.

In some examples, the system 500 may allow the clinician to select a particular body region from amongst the body regions. Upon selecting the particular body region, the system 500 may identify at least one representation, and request the clinician to capture an image (e.g., captured image 700) or select a default image (e.g., default image 800) (S510). In the case that the clinician selects to capture an image, the clinician may be prompted by the system 500 to capture an image, as depicted in UI305 and UI310. Once the clinician has captured the image, they may view and/or manipulate the captured image, as depicted in UI315, and/or the default image as shown in UI317.

In some examples, the system 500 may further identify one or more icons for displaying to the user (S515) as depicted in UI405, and allow the user to select an icon for defining on the captured image, as depicted in UI410, and/or default image as depicted in UI412 (S520). The system 500 may allow a clinician to select an icon, such as with a finger and/or stylus, and define the selected icon on a portion of the captured image and/or default image, such as on a cutaneous condition(s) represented in the captured image and/or default image. The system 500 may further allow the user to define a boundary (e.g., second outline 720B and second outline 820B) around an area that may be affected by a cutaneous condition, and/or the cutaneous condition itself (e.g., first outline 720A and first outline 820A).

In some examples, the system 500 may allow the clinician to select a defined icon, and render a details panel (e.g. details panel 900) of the cutaneous condition corresponding to the defined icon, as depicted in UI505. Similarly, the system 500 may allow the clinician to select a defined boundary corresponding to a cutaneous condition, and render a details panel of the cutaneous condition. The system may further allow the clinician to select a defined boundary corresponding to the are affected by a cutaneous condition, and render a details panel of the affected area, as depicted in UI510.

In some examples, in the case that one or more cutaneous condition(s) represented in the captured image and/or default image is to be intervened upon during the evaluation of the patient, the evaluating clinician may indicate that an intervention has been performed upon the intervened cutaneous condition(s) via the details panel corresponding to that particular cutaneous condition(s). As depicted in UI605, the clinician may indicate that an intervention has been performed by toggling a virtual switch and selecting an intervention type (e.g., intervention indicator 620A). As depicted in UI610, the defined icon corresponding to intervened cutaneous condition(s) may be visually different from a defined icon corresponding to cutaneous condition(s) that have not been intervened upon. Similarly, as depicted in UI615, a defined boundary corresponding to a cutaneous condition(s) that has been intervened upon may be visually different from a defined boundary corresponding to a non-intervened cutaneous condition.

In some examples, once an intervention has been indicated by the clinician, the system 500 may store details regarding the intervention conducted, and display details of the intervention within the details panel as depicted in UI705. During a subsequent evaluation, if the evaluating clinician attempts to complete the evaluation without defining an icon on the intervened cutaneous condition(s) and/or indicating that the cutaneous conditions have been previously intervened upon, the system 500 may prompt the clinician to address the intervened cutaneous conditions with respect to the subsequent evaluation, as depicted in UI710.

According to various embodiments of the present disclosure, the system 500 is implemented using one or more processing circuits or electronic circuits configured to perform various operations as described above. Types of electronic circuits may include a central processing unit (CPU), a graphics processing unit (GPU), an artificial intelligence (AI) accelerator (e.g., a vector processor, which may include vector arithmetic logic units configured efficiently perform operations common to neural networks, such as dot products and softmax), a field programmable gate array (FPGA), an application specific integrated circuit (ASIC), a digital signal processor (DSP), or the like. For example, in some circumstances, aspects of embodiments of the present disclosure are implemented in program instructions that are stored in a non-volatile computer readable memory where, when executed by the electronic circuit (e.g., a CPU, a GPU, an AI accelerator, or combinations thereof), perform the operations described. The operations performed by the system 500 may be performed by a single electronic circuit (e.g., a single CPU, a single GPU, or the like) or may be allocated between multiple electronic circuits (e.g., multiple GPUs or a CPU in conjunction with a GPU). The multiple electronic circuits may be local to one another (e.g., located on a same die, located within a same package, or located within a same embedded device or computer system) and/or may be remote from one other (e.g., in communication over a network such as a local personal area network such as Bluetooth®, over a local area network such as a local wired and/or wireless network, and/or over wide area network such as the internet, such a case where some operations are performed locally and other operations are performed on a server hosted by a cloud computing service). One or more electronic circuits operating to implement the system 500 may be referred to herein as a computer or a computer system, which may include memory storing instructions that, when executed by the one or more electronic circuits, implement the systems and methods described herein.

The terminology used herein is for the purpose of describing particular embodiments only and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

It will be understood that the example embodiments described hereinabove are merely exemplary and that a person skilled in the art may make many variations and modifications without departing from the spirit and scope of the present invention. All such variations and modifications are intended to be included within the scope of the invention as defined in the accompanying claims.

What is claimed is:

1. A system for mapping one or more cutaneous conditions of a cutaneous surface, the system comprising:

at least one processor, at least one display, the at least one display configured to receive user input, and operatively connected to the at least one processor; and a memory, the memory operatively connected to the at least one processor and storing instructions that, when executed, cause the at least one processor to perform a method, the method comprising:

identifying a body map;

identifying one or more body regions corresponding to the body map;

identifying at least one representation corresponding to the one or more body regions;

identifying one or more icons corresponding to the at least one represen- tation;

defining the one or more icons on the at least one representation;

detecting a placement of the one or more icons; and overlaying the one or more icons on the at least one representation based on the placement of the one or more icons.

2. The system of claim 1, wherein the system further comprises:

at least one camera, the at least one camera operatively connected to the at least one processor.

3. The system of claim 1, wherein the body map comprises one or more multi-dimensional renderings.

4. The system of claim 1, wherein the at least one representation comprises one or more images.

5. The system of claim 1, wherein the method performed by the at least one processor further comprises:

identifying a patient profile; and generating the body map based on the patient profile.

6. The system of claim 1, wherein the method performed by the at least one processor further comprises:

detecting the one or more body regions based on the body map; and defining the one or more body regions on the body map.

7. The system of claim 1, wherein the method performed by the at least one processor further comprises:

generating the one or more icons; and rendering the one or more icons while simultaneously rendering the at least one representation.

8. The system of claim 1, wherein the method performed by the at least one processor further comprises:

detecting the one or more icons from a selection of icons; and rendering the one or more icons while simultaneously rendering the at least one representation.

9. The method of claim 1, wherein the defining the one or more icons comprises:

placing a first boundary around a first one of the one or more cutaneous condi- tions to form a first enclosed area; and placing a second boundary around a second one of the one or more cutaneous conditions to form a second enclosed area.

10. The method of claim 9, wherein the first boundary or the second boundary are placed based on an external input.

11. The method of claim 9, wherein the defining the one or more icons further comprises:

defining a first color on at least a portion of the first enclosed area; and defining a second color on at least a portion of the second enclosed area.

12. The method of claim 1, wherein the defining the one or more icons comprises:

identifying a first color corresponding to the first one of the one or more cutaneous conditions; and identifying a second color corresponding to the second one of the one or more cutaneous conditions, wherein the first color is different from the second color.

13. A method for mapping one or more cutaneous conditions of a cutaneous surface, the method comprising:

identifying a body map;

identifying one or more body regions corresponding to the body map;

identifying at least one representation corresponding to the one or more body re- gions;

identifying one or more icons corresponding to the at least one representation; and defining the one or more icons on the at least one representation;

wherein the defining the one or more icons comprises:

detecting a placement of the one or more icons; and overlaying the one or more icons on the at least one representation based on the placement of the one or more icons.

14. The method of claim 13, wherein the body map comprises one or more multi-dimensional renderings.

15. The method of claim 13, wherein the at least one representation comprises one or more images.

16. The method of claim 13, wherein the identifying the body map comprises: identifying a patient profile; and generating the body map based on the patient profile.

17. The method of claim 13, wherein the identifying the one or more body regions comprises:

detecting the one or more body regions based on the body map; and defining the one or more body regions on the body map.

18. The method of claim 13, wherein the identifying the one or more icons comprises:

generating the one or more icons; and rendering the one or more icons while simultaneously rendering the at least one representation.

19. The method of claim 13, wherein the identifying the one or more icons comprises:

detecting the one or more icons from a selection of icons; and rendering the one or more icons while simultaneously rendering the at least one representation.

20. The method of claim 13, wherein the at least one representation is captured by at least one camera.

21. The method of claim 13, wherein the at least one representation comprises at least one of a captured representation or default representation.

22. The method of claim 13, the method further comprising:

identifying at least one of a first captured representation or a first default representation, the at least one of the first captured representation or the first default representation corresponding to a first evaluation;

identifying at least one of a second captured representation or a second default representation, the at least one of the second captured representation or the second default representation corresponding to a second evaluation; and rendering the at least one of the first captured representation or the first default representation and the at least one of the second captured representation or the second default representation.

23. The method of claim 22, wherein the at least one of the first captured representation or the first default representation is selectively rendered with the at least one of the second captured representation or the second default representation based on user input.

24. The method of claim 22, wherein the at least one of the first captured representation or the first default representation is simultaneously rendered with the at least one of the second captured representation or the second default representation based on user input.

25. A method for mapping one or more cutaneous conditions of a cutaneous surface, the method comprising:

identifying a first representation corresponding to one or more body regions of the cutaneous surface;

identifying a second representation corresponding to the one or more body regions of the cutaneous surface;

identifying a ghost representation based on the first representation;

overlaying the ghost representation on the second representation of the cutaneous surface; and mapping the one or more cutaneous conditions using the ghost representation overlayed on the second representation.

26. The method of claim 25, wherein the ghost representation comprises one or more images.

27. The method of claim 25, wherein the first representation comprises one or more images.

28. The method of claim 25, wherein the second representation comprises one or more images.

* * * * *